US012233213B1

(12) United States Patent
Sabin

(10) Patent No.: US 12,233,213 B1
(45) Date of Patent: Feb. 25, 2025

(54) INHALED INTERNAL HEAT/THERMAL CONDUCTION THERAPY FOR ESOPHAGEAL CANCER

(71) Applicant: Robert Sabin, Mill Neck, NY (US)

(72) Inventor: Robert Sabin, Mill Neck, NY (US)

( * ) Notice: Subject to any disclaimer, the term of this patent is extended or adjusted under 35 U.S.C. 154(b) by 0 days.

(21) Appl. No.: 18/801,599

(22) Filed: Aug. 12, 2024

Related U.S. Application Data

(63) Continuation-in-part of application No. 18/600,704, filed on Mar. 9, 2024, now Pat. No. 12,083,040, which is a continuation-in-part of application No. 18/432,843, filed on Feb. 5, 2024, now Pat. No. 12,004,993, which is a continuation-in-part of application No. 18/418,179, filed on Jan. 19, 2024.

(51) Int. Cl.
| *A61F 7/12* | (2006.01) |
| *A61F 7/00* | (2006.01) |
| *A61F 7/02* | (2006.01) |
| *A61M 16/10* | (2006.01) |

(52) U.S. Cl.
CPC ....... *A61M 16/1095* (2014.02); *A61F 7/0085* (2013.01); *A61F 7/12* (2013.01); *A61F 2007/006* (2013.01); *A61F 2007/0086* (2013.01); *A61F 2007/0093* (2013.01); *A61F 2007/0096* (2013.01); *A61M 2205/3368* (2013.01); *A61M 2205/362* (2013.01); *A61M 2210/1032* (2013.01); *A61M 2210/105* (2013.01); *A61M 2230/50* (2013.01)

(58) Field of Classification Search
CPC ........ A61F 2007/0052; A61F 2007/006; A61F 2007/0086; A61F 2007/0087; A61F 2007/0093; A61F 2007/0096
See application file for complete search history.

(56) References Cited

U.S. PATENT DOCUMENTS

2018/0325817 A1* 11/2018 Batchinsky .......... A61K 9/0078
2020/0206442 A1* 7/2020 Knepper ........... A61M 16/0616
2021/0282964 A1* 9/2021 Sabin ................ A61M 16/1095

OTHER PUBLICATIONS

Raiko_Imaging-based-internal-body-temp-measurements-the-journal-temp-toolbox_TEMPERATURE_Vol7no4_KTMP_7_1769006_26-pp_2020.

(Continued)

*Primary Examiner* — Tigist S Demie
(74) *Attorney, Agent, or Firm* — Alfred M Walker

(57) ABSTRACT

A method for treating esophageal cancer in situ with heated air that can be inhaled through a face mask, at an elevated temperature less than sauna air temperatures and at a constant positive air pressure. The inhaled heated air will heat the very thin tracheoesophageal party wall sheath membrane between the esophagus and the respiratory trachea in the throat. The tracheoesophageal party wall sheath membrane therefore can heat the esophageal cancer tumor adjacent to the heated trachea and tracheoesophageal party wall sheath membrane. The heated air will be inspired/inhaled through the mouth and into the trachea/windpipe. Then the trachea and trachea tube under heated constant positive pressure will then transfer heat through and to the esophagus wall, and esophagus and tumor. The heat from the heater air inspiration through the trachea migrates/transmits/disperses across the membrane separating the trachea/windpipe from the esophagus and hits the esophagus with heat.

7 Claims, 9 Drawing Sheets

(56) References Cited

OTHER PUBLICATIONS

National_Cancer_Institute_"Hyperthermia to treat cancer,"_at_cancer.gov/about-cancer/treatment/types/hyperthermia_9-pp_2023.
Mayo_Clinic_Esophageal_cancer_7-pp_2024.
Mount_Sinai_Esophageal_Cancer_4-pp_2024.
Katsarelias_"The-Effect-of-Temperature-and_Perfusion-time-on-Response-Toxicity-and-Survival-in-Patients-with-In-transit-Melanoma-Metastases-Treated-with-Isolated-Limb-Perfusion"_Ann-Surg-Oncol_2018_25(7)_1836-1842_May_15_2018_7-pp.
American_Cancer_Society_(ACS)_Treating-Esophagus-Cancer_2-pp_2024.
Cleveland-Clinic_October_18_2018_Hyperthermia-Why-Heat-Can-Make-Cancer-Treatments-More-Potent_13-pp.
Master-ProHeat-1400A-Digital-Professional-Heatgun-&-Kit_7-pp_website_catalog_2024.

\* cited by examiner

Fig. 1
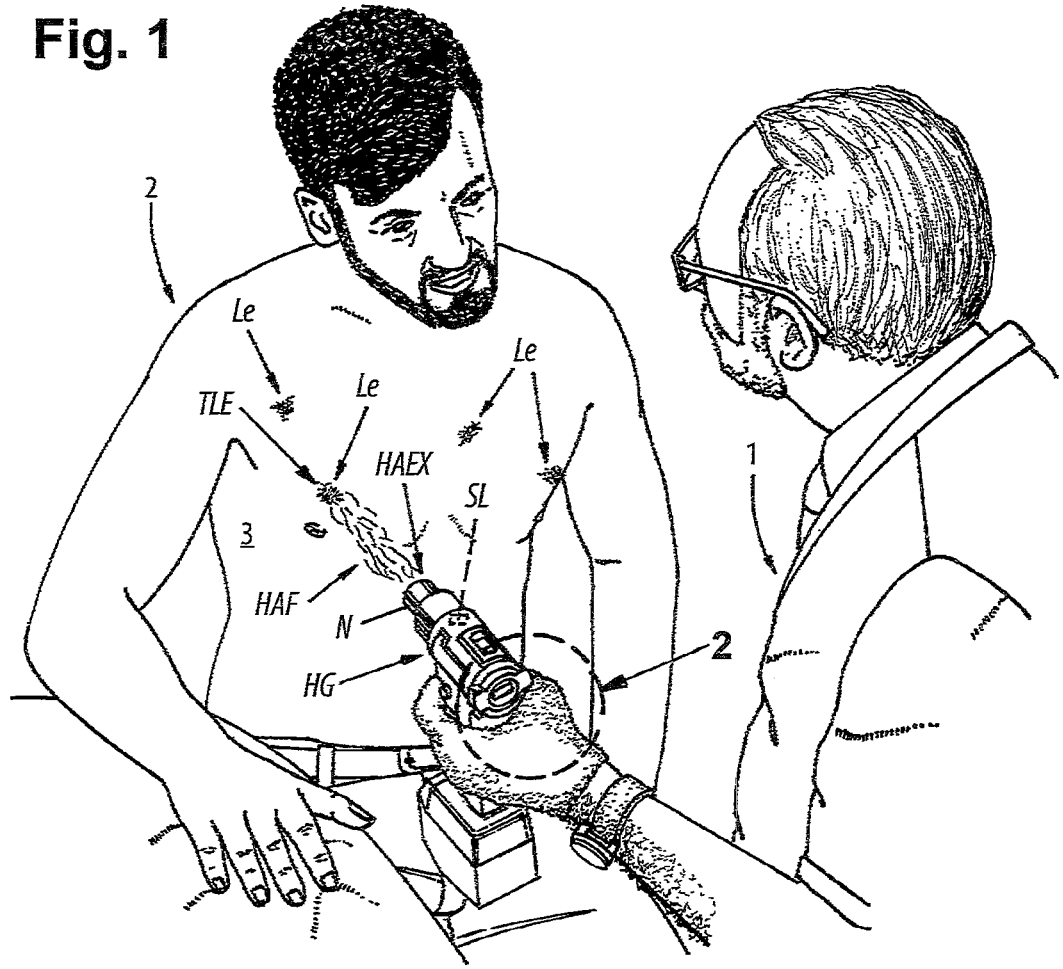
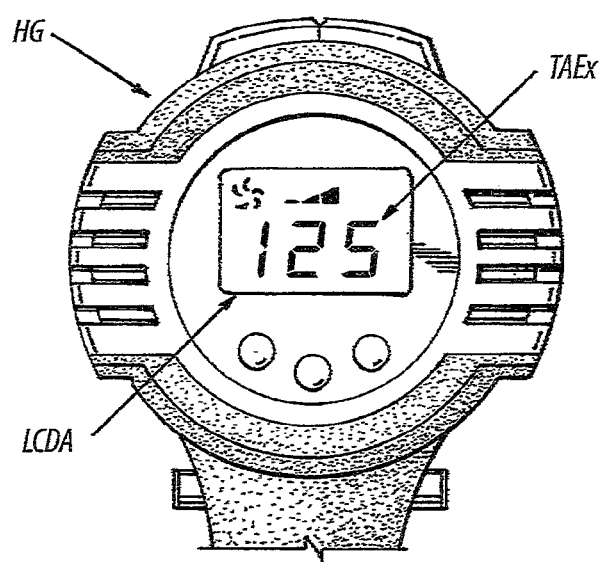
Fig. 2

INHALED INTERNAL HEAT/THERMAL CONDUCTION THERAPY FOR ESOPHAGEAL CANCER

RELATED APPLICATIONS

This application is a continuation-in-part of application Ser. No. 18/600,704, filed Mar. 9, 2024, which '704 application is a continuation-in-part of application Ser. No. 18/432,843, filed Feb. 5, 2024, now U.S. Pat. No. 12,004,993 B1 issued Jun. 11, 2024, for a TOPICALLY APPLIED HEAT/THERAPY FOR SKIN LESIONS AND OTHER DISEASES, which '843 application is a continuation-in-part of application Ser. No. 18/418,179, filed Jan. 19, 2024, which '704, '843 and '179 applications are incorporated by reference herein. Applicant claims priority under 35 U.S.C. § 120 from the '704, '843 and '179 applications.

INCORPORATION BY REFERENCE

This application incorporates by reference in its entirety Applicant's U.S. Pat. No. 12,004,993 B1 issued Jun. 11, 2024, entitled TOPICALLY APPLIED HEAT/THERAPY FOR SKIN LESIONS AND OTHER DISEASES, and which '993 Patent was filed under USPTO application Ser. No. 18/432,843 on Feb. 5, 2024. This application also incorporates by reference in its entirety Applicant's U.S. Pat. No. 11,234,861 B2 issued Feb. 1, 2022, entitled RESPIRATORY THERAPEUTIC ELECTRIC HEAT SOURCE FACE MASK, and which '861 Patent was filed under USPTO application Ser. No. 17/337,352 on Jun. 2, 2021, which '352 application was published as US 2021/0282964 A1 on Sep. 16, 2021. This application also incorporates by reference in its entirety Applicant's U.S. Pat. No. 10,905,585 B1 issued Feb. 2, 2021, entitled RESPIRATORY THERAPEUTIC ELECTRIC HEAT SOURCE FACE MASK, and which '585 Patent was filed under USPTO application Ser. No. 16/893,212 on Jun. 4, 2020.

FIELD OF THE INVENTION

The present invention relates to treating esophageal cancer in situ with heated air that can be inhaled through a "mister", like nebulizer inhaler machines used to treat asthma, at an elevated temperature less than sauna air temperatures. The inhaled heated air will heat the very thin tracheoesophageal party wall sheath membrane between the esophagus and the respiratory trachea in the throat. The tracheoesophageal party wall sheath membrane therefore can heat the esophageal cancer tumor adjacent to the heated trachea and tracheoesophageal party wall sheath membrane, without the need for sedation of the patient during the invasive procedures currently used surgically.

BACKGROUND OF THE INVENTION

All references are included in their entirety as if reproduced in full herein.

In Cleveland Clinic, Esophageal Cancer, 2024, esophageal cancer is defined as tumors within the esophagus between the mouth and stomach of a person, and being either adenocarcinomas in the lower part of the esophagus and Squamous cell carcinomas that affect the squamous cells lining the esophagus. Symptoms and causes of esophageal cancer are discussed, as are diagnostic tools for detecting esophageal cancer. Treatment regimens are discussed, including surgery, radiation therapy, chemotherapy, endoscopic submucosal dissection (ESD) or endoscopic mucosal resection (EMR), endoscopic laser therapy, photodynamic therapy (PDT), targeted HER2 protein therapy and immunotherapy. Lifestyle alternatives are also discussed to reduce the possibility of esophageal cancer.

Mount Sinai Esophageal Cancer, 2024, discusses esophageal cancer in general.

American Cancer Society (ACS) in "Treating Esophagus Cancer", 2024, discloses local and systemic treatment options for patients with Esophageal Cancer.

Mayo Clinic, in Esophageal cancer, 2024, discusses various treatment regimens for treating esophageal cancer.

Esophageal cancer can be treated with heat in situ. See National Cancer Institute "Hyperthermia to treat cancer," at cancer.gov/about-cancer/treatment/types/hyperthermia. NCI discloses that temperature at about 113° F. kills cancer cells with little or no harm to normal human body tissue. The New York Times, opus cited, at page 3/9, discloses that treating human tissue topically at 50° C., for 30 seconds 122° F., kills the parasite/Leishmaniasis protozoa deep inside the human tissue.

See also Daniel Yetman, "Hyperthermia Treatment for Cancer: Uses and Effectiveness", Healthline Newsletter, Nov. 9, 2022 (reviewed by Teresa Hagan Thomas). Yetman discloses that temperatures of 106° F. to 111° F. are toxic to cancer cells while sparing normal cells.

Saunas have been used for thousands of years. See Wikipedia at "The Finnish Sauna". The earliest versions date from 7000BC. Millions of people have used them in the intervening years with great safety. The sauna room, which is the sauna, is generally warmed to 176-230° F., op cit. The sauna room exposes the entire body to the heat.

"The Physics Factbook", edited by Glen Elert, discloses different ranges of temperatures of Sauna units, at 176-212° F., 150-194° F., 170-180° F., and 160° F.

"Emma, in "Ideal Sauna Temperatures: How Hot Is Your Sauna?", website, 2020 discloses the Finnish sauna temperature is typically 160-194° F. for 30 to 45 minutes. It also discloses that "the American standard implies temperatures from 160 to 194° F., but in many European countries, allowed temperatures are in the range of 160 to 220° F." and, "However, the Finnish Sauna Society recommends that the temperature in the sauna should be from 176 to 194° F. (80-90° C.) with the ultimate maximum of 212° F. (100° C.").
]

Thermoregulation" Healthline, discloses that sweat cools human skin as it evaporates, and that the hypothalamus sends signals to various organs and systems in the body.

The skin's immense blood supply helps regulate temperature: i.e., dilated vessels/capillaries near the surface of the skin allow for heat loss through the blood, through sweating, while constricted vessels retain heat. The skin regulates body temperature with its blood supply, elevated by temperatures, which are expelled through sweat from the skin with its large surface area. Humidity affects thermoregulation by limiting sweat evaporation and thus heat loss.

Without being limited, held, or bound, this is the critical inventive step of the invention. For example, the sauna will not raise the temperature of lung tissue very much, as it is analogous to pouring water into a bucket with no bottom. In the sauna, the entire skin is exposed to heat, opening the pores to expel sweat and heat derived from the enormous blood supply trafficking throughout the body and skin. However, in contrast, the Applicant's invention isolates the respiratory system from the rest of the body and skin so that the respiratory and heated lung tissue generated through the face mask, will disperse/exit more slowly, allowing an elevated tissue temperature in the lung. Instead of having a bucket with no bottom, now there is a bucket with holes in the bottom to drain water out more slowly, allowing a higher lung tissue temperature.

Moreover, "National Cancer Institute" in Hyperthermia in Cancer Treatment" discloses: "Hyperthermia (also called thermal therapy or thermotherapy) is a type of cancer treatment in which body tissue is exposed to high temperatures (up to 113° F.). Research has shown that high temperatures can damage and kill cancer cells, usually with minimal injury to normal tissues (1). By killing cancer cells and damaging proteins and structures within cells (2), hyperthermia may shrink tumors."

This is the "holy grail" of cancer medicine that is most earnestly pursued or sought after. Despite many decades of research, exploitable differences between normal cells and cancer cells remain elusive. Very few, if any, differences exist in tumor and normal cell antigens for targeting. The massive difference in the uptake of glucose by tumor cells against normal cells is one. This resulted in the well-known Positive Emission Tomography (PET Scan). Drugs are currently being designed to support this major exploitable difference in glucose uptake. The differential in sensitivity to heat is another holy grail of cancer medicine, which the Applicant utilizes to treat tumors and dysplasia in the lung.

Cleveland Clinic, Oct. 18, 2018, discloses "Hyperthermia: Why Heat Can Make Cancer Treatments More Potent". They use the application of heat at 109-110° F. with radiation and chemotherapy.

Moreover, Katsarelias, et al, in "The Effect of Temperature and perfusion time on Response, Toxicity and Survival in Patients with In-transit Melanoma Metastases Treated with Isolated Limb Perfusion", Ann Surg Oncol: 2018; 25 (7): 1836-1842 May 15, 2018, discloses a well-established technique to administer "a very high dose" of chemotherapy, at elevated temperature, to isolated tumor sites without causing overwhelming systemic damage.

Also, the Cleveland Clinic, in "Hyperthermia: Why Heat Can Make Cancer Treatment More Potent—Combing heat with chemo or radiation can shrink tumors" Cleveland Clinic Cancer Care website, Oct. 18, 2018, states that heat can be combined with chemotherapy or radiation therapy to reduce or destroy cancer tumor cells.

Additionally, NIH National Cancer Institute, in "Hyperthermia in Cancer Treatment", Aug. 31, 2011, disclosed that hyperthermia cats in combination with chemotherapy and/or radiation can damage cancer cells and enhance the antitumor effects of chemotherapy and/or radiation." Further disclosed is that at 113° F., tumor cells are harmed and killed, leaving normal cells unscathed.

Applicant's prior art U.S. Pat. No. 11,234,861 B2 issued Feb. 1, 2022, entitled RESPIRATORY THERAPEUTIC ELECTRIC HEAT SOURCE FACE MASK discloses administering controlled heat from a heat gun through a mask, to provide heated air to treat respiratory diseases.

Raiko et al, in Imaging based internal body temperature measurements, in the Journal of "temp-toolbox" in TEMPERATURE, Vol 7, no. 4 at KTMP 71769006, discloses non-invasive temperature measurements of internal body tissues.

OBJECTS OF THE INVENTION

It is therefore an object of the present invention to provide heated air that can be inhaled through a "mister" like asthma inhalers, at an elevated temperature less than sauna air temperatures. The inhaled heated air will heat the very thin tracheoesophageal party wall sheath membrane between the esophagus and the respiratory trachea in the throat. The tracheoesophageal party wall sheath membrane therefore can heat the esophageal cancer tumor adjacent to the heated trachea and tracheoesophageal party wall sheath membrane, without the need for sedation of the patient during the invasive procedures currently used surgically.

The heat from the heater air inspiration through the trachea migrates/transmits/disperses across the membrane separating the Trachea/windpipe from the esophagus and hits the esophagus with heat.

It is also very desirable to have the heated air being delivered by a handheld, battery powered or powered by 120 V utility power heat gun with safety locks, operable for heat treatment of esophageal cancers in real time, which is way less toxic, less painful, more efficacious, quicker, and which operates at a higher temperature, and is cost effective. Moreover, the higher temperatures available facilitate treatment of esophageal cancerous tumors by delivering heated air through a face mask directly delivering the heated air to a cancer patient's throat tracheas so that the heated air will conductively heat the cancerous esophageal tumor by passing through the tracheoesophageal party wall sheath membrane, to the esophageal tumor in the esophagus, on the adjacent opposite side of the tracheoesophageal party wall sheath membrane.

It is also an object to provide a cost-effective battery or AC powered heated air delivery machine, and where the cost of use is a small fraction of the cost of existing invasive endoscopic devices, and without costly maintenance.

Other objects of the invention will become apparent from the following description of the present invention.

SUMMARY OF THE INVENTION

The present invention relates to treating esophageal cancer in situ with heated air that can be inhaled through a "mister" like asthma inhalers, at an elevated temperature less than sauna air temperatures. The inhaled heated air will heat the very thin tracheoesophageal party wall sheath membrane between the esophagus and the respiratory trachea in the throat. The tracheoesophageal party wall sheath membrane (also known as the "membranous trachea") therefore can heat by conduction the esophageal cancer tumor adjacent to the heated trachea and tracheoesophageal party wall sheath membrane, without the need for sedation of the patient during the invasive procedures currently used surgically.

The heat from the heater air inspiration through the trachea migrates/transmits/disperses heat via conduction across the tracheoesophageal party wall sheath membrane separating the trachea/windpipe from the esophagus and hits the esophagus with heat.

The heated air will be inspired/inhaled through the mouth and into the trachea/windpipe. Then the trachea and trachea tube under heated constant positive pressure will then transfer heat through and to the esophagus wall, and esophagus and tumor.

The esophagus parallels the trachea/windpipe, the wall of the trachea is very close to the wall the inner wall of the esophagus.

Then it follows by inhaling/inspiring heated air up to 180 degrees F. with the invention, it is possible enough heat will emanate/traffic by heat conduction from the trachea/windpipe wall and conductively interface with the esophagus wall and esophagus. Therefore, the inhaled heat within the trachea migrates across the tracheoesophageal party wall sheath membrane, separating the trachea/windpipe from the esophagus and via conduction the inhaled heat in the trachea/windpipe raises the heat of the localized esophageal tumor at a threshold of about 113 degrees F., which will kill cancer in the esophagus by apoptosis, known S programmed tumor cell death.

As disclosed in Raiko_Imaging-based-internal-body-temp-measurements-the-journal-temp-toolbox_TEMPERATURE_Vol7no4_KTMP_7_1769006, in order to non-invasively and remotely measure the temperature of the cancer cells being annihilated by apoptosis caused by pre-determined time exposure to the conducted heat through the membrane separating the trachea/windpipe from the esophageal tumor site within the esophagus, external probes using external image-based internal body temperature measurements can be administered, such non-invasive devices as ultrasound, magnetic resonance imaging, computed tomography, microwave radiometry, photoacoustic imaging and near-infrared spectrometer, either within a hollow cavity such as CT scan or MRI imaging tunnel machine, or by a hand-held device such as an ultrasound transducer used in combination with a pulsed laser light source provided built into the heat source heat gun, or via a separate handheld measurer such as an ultrasound transducer, where the raised temperature within the tissues of the esophageal tumor can be measured and displayed on a display device, such as on the heat gun or on a display of the remote handheld device or imaging tunnel device.

Applicant's U.S. Pat. No. 11,234,861 B2 "Respiratory Therapeutic Electric Heat Source Face Mask", dated Feb. 1, 2022, and its parent U.S. Pat. No. 10,905,585 B1 "Respiratory Therapeutic Electric Heat Source Face Mask", dated Feb. 2, 2021, are both incorporated by reference herein in their entirety, for information about heated air sources, such as heat guns, with air temperature safety locks and interlocks providing controlled and monitored application of hot air into the respiratory system of a patient, without exceeding a predetermined safe temperature threshold of hot air. These heat guns disclosed in these patents can also be used, although they require a 120 Volt plug in power supply.

To treat esophageal tumors adjacent to the tracheoesophageal party wall sheath membrane separating the trachea from the esophagus, the Applicant's device can be placed directly over the patient's mouth to introduce treated air to the trachea. The method of treatment includes the steps of;

a) placing a concentrated but efficacious quantity of heated air generated by a heat source through a face mask having an outlet tube within the trachea of a patient, adjacent to the tracheoesophageal party wall sheath membrane, spaced from an esophageal cancer on and/or extending within the esophagus of the patient;

b) directing the efficacious applied heated air from the heat source into the trachea, to conductively transfer the heated air of the heat source, through the tracheoesophageal party wall sheath membrane, thereby directly to the esophageal cancer tumor adjacent thereto;

c) applying the efficacious exterior topically applied heated air directed from the heat source to a full area of the cancer on or within the esophagus;

d) programming the heat source for producing and directing the efficacious exterior topically applied heated air having a temperature sufficient for, and for a sufficient time, at a constant air pressure, to destroy the cancer on and/or extending within the esophagus of the patient;

e) monitoring the heat source and constant air pressure for insuring that the efficacious inhaled heated air being delivered to the cancer through the tracheoesophageal party wall sheath membrane does not exceed a predetermined safe temperature threshold of the inhaled heated air; and, f) mounting a display on or adjacent the heat source showing the set programmed temperature and a current temperature of the esophageal tumor cancer being treated, the cancer located within or on the esophagus in the vicinity of the tracheoesophageal party wall sheath membrane separating the esophagus from the trachea of the patient.

Therefore, the heat from the heated air traverses through the trachea and conductively migrates/transmits/disperses across the tracheoesophageal party wall sheath membrane separating the trachea/windpipe from the esophagus and directly contacts the esophagus with heat at a constant air pressure.

The method further includes the heat source preferably being a heat gun with an outlet nozzle sufficiently large and shaped to deliver the heated air through the face mask into the patient's trachea, wherein a display on the heat gun comprises an LCD screen showing both of the temperatures, including the set programmed temperature of the heated air and optionally the remotely determined current temperature at a surface of the esophageal cancer located adjacent to the trachea of the patient. The set programmed temperature is displayed on an upper portion of the screen and a current cancerous tumor temperature is remotely displayed on another display screen.

The method includes further optionally using a laser infrared light beam or ultrasound transducer projected at or above the site of the esophageal cancer for measuring the temperature of the cancerous tumor, to determine the temperature of the esophageal cancer when being subject to apoptosis programmed cell death.

The heat gun has different sized nozzles, for delivery of the applied heated air to the cancer located on or within the esophagus of the patient, at or adjacent to the surface of the tracheoesophageal party wall sheath membrane of the patient, preferably in the range of about 113 degrees F., to about 140+ degrees F., where 113 degrees F. has been described in the literature known to those skilled in the art of cancer treatment as being the minimal temperature for subjecting the cancerous esophageal tumor to apoptosis programmed cell death.

A further option includes the step of inserting a subcutaneous needle probe temperature monitor into the in-situ site of the esophageal tumor being treated and measuring the temperature of the tumor being treated.

Because coffee and hot chocolate are served between 160° F.-185° F. of heat to billions of people for many decades without burning the mouth, then it is reasonable that Applicant's invention can be applied at 140+° F. of heat through the trachea of the patient to the tumor or cancer.

Applicant has heard a number of times whereby a surgeon opens up a cancer patient's torso, and gasps nothing to be done, extensive disease, or looked at an x ray with the same conclusion. Now, with the applicant's invention, the surgeon can avoid surgically opening a patient's chest, abdomen, etc., and using the applicant's invention, he or she can kill the esophageal cancer cells, in a brief time, since the application of heated air at 113° F. is known to kill tumor cells.

As taught by Raiko, et al, op cit., the method of Applicant's invention includes an option of using a temperature monitored application of hot air to the transfer of the patient, where the threshold temperature of the patient's esophageal tumor is measured and monitored by either built-in laser infrared temperature sensor features, or by remote handheld non-contact, infrared-based skin lesion thermometers during the procedure, in order to inactivate the tumor by apoptosis, programmed tumor cell death.

An example of a preferred embodiment for the heat source is a heat gun, which uses nozzles for aiming monitored hot air flow, with built-in safety locks and interlocks, but which also has a built-in laser infrared temperature sensor and LCD display, such as is manufactured by Master Heat Tools, as MASTER PROHEAT STC®, which is a surface temperature control heat gun. This heat gun can dispense hot air through the face mask tube to the trachea of a patient at specified exiting air temperatures, so that the esophageal cancer is treated at a predetermined temperature to inactivate the cancerous tumor, which is located adjacent to the tracheoesophageal party wall sheath membrane separating the trachea through which the hot air is delivered, from the esophageal tumor, which is conductively heated by the heated air in the trachea transversing therethrough to the adjacent esophageal tumor.

The preferred range of the skin temperature being treated can be preferably in the range of about 113 degrees F. up to about 140+ degrees F., such as about 120 degrees F. to about 130 degrees F.

The Applicant's invention can use the aforementioned infrared based, non-contact thermometers, or other temperature monitoring devices described by Raiko, et al, op cit. to remotely determine the temperature of the cancerous tumor, when the medical practitioner is holding a heat gun, which has a LCD display, but which can indicate the temperature of the heated air coming out of the heat gun, but optionally the remote temperature sensor described in Raiko et al can remotely measure the temperature of the esophageal tumor being treated.

Applicant also submits the following reference for incorporation by reference in its entirety, entitled "Cordless heat gun for Milwaukee 18v battery, Mtiolhig portable 112° F. to 1022° F. battery powered heat shrink gun with 5 pcs nozzles for crafts, shrink tubing, vinyl wrap, paint removal." There are also quick connect nozzle kits with many different size nozzles available on Amazon.

Therefore, the present invention preferably utilizes no invasive endoscopic device, with possible pain and internal injuries. Second, the heated air derived from the applicant's inventions covers the entire esophageal tumor at one time, beginning to end, without invasively needing sedation and an endoscopic probe within the patient's esophagus.

In contrast to endoscopic procedures, the present invention monitors and regulates the temperature of the esophageal tumor being treated. The heated air flow of the Applicant's invention may be raised and lowered by pressing control buttons on the heat source, which is preferably a heat gun with built in safety locks to prevent inadvertent excess heat and air pressure being administered to the esophageal tumor adjacent to the aforementioned tracheoesophageal party wall sheath membrane of the patient.

For example, Applicant's heat gun can be, preferably, battery powered and portable. If utility power such as 120 Volts is available, the heat gun can be powered by utility power as well.

In summary, the aforementioned administration of applicant's invention herein includes the inhaled administration of temperature controlled heated air to the trachea of the patient, with a concentrated inhaled heat source, for destroying esophageal tumors located in the esophagus adjacent to the tracheoesophageal party wall sheath membrane separating the trachea of the patient from the closely adjacent esophagus of the patient.

As noted above, the inhaled hot air applied to the trachea of the patient is adjusted upward to a temperature of the esophageal tumor being treated, where the temperature is adjusted upward from about 120 degrees F. to about 130 degrees F., to have a net temperature of about at least 113 degrees F. at the esophageal tumor.

In a preferred embodiment for treating esophageal cancer, the method steps further include the following details:
 a) install a correct nozzle on the heat gun;
 b) determine and adjust the temperature of the airflow;
 c) program and provide the heated hot air flow at a threshold temperature of an esophageal tumor sufficient to remove the esophageal tumor;
 d) adjust the output nozzle of applicant's heat gun and supply hot air through the patient's mouth and trachea to a location of the thin tracheoesophageal party wall sheath membrane separating the trachea from the esophagus in the vicinity of the esophageal tumor;
 e) activate the temperature-controlled heat gun with locks and interlocks, at which time the entire tumor will be conductively heated across the thin tracheoesophageal party wall sheath membrane from the trachea into the esophagus with heat derived from hot air at constant air pressure and controlled threshold temperatures; and,
 f) monitoring the tumor temperature for ensuring that the heated air does not exceed a safe temperature threshold within the trachea and esophagus of the patient.

As noted in Applicant's prior art U.S. Pat. No. 11,234,861 B2, while the power source for the heat gun is preferably AC power, optionally the power source can alternatively be a low voltage DC power source, such as a battery, or the power source can be AC power transformed to a low voltage DC power source.

Preferably, the prior art of Sabin '861 heat gun heats air to a sufficiently high temperature is between about at least 80 degrees F. and about 275 degrees F., optionally, in which the sufficiently high temperature is at least 113 degrees F. up to about 230 degrees F. Also, optionally, the humidity is preferably about 90 to 95%, which is maintained by human respiration in the throat of a person being treated.

In order to keep the pressure of the heated air at a tolerable level compatible with human respiration, the air pressure of the heated air is compatible with typical air pressure flows in a Continuous Positive Air Pressure (CPAP) machine. Most CPAP machines pump air in the range from 6 to 15 cm/H2O (centimeters of water pressure), such as, for example, an air flow is set at 8 cm/H2O.

To convert that to air pressure measured in millimeters of mercury (Hg), one divides the cm/H2O amount by a factor of 1.36. Therefore, a CPAP air flow pressure of 8 cm/$H_2$O is divided by a factor of 1.36, wherein 8/1.36=5.88 Hg. Stated in psi (pounds per square inch), an 8 cm/H2O=5.88 Hg, or 2.88 psi.

Even at the upper limit of 15, the air pressure being pumped from a CPAP machine into the person is only 11 Hg, or 5.4 psi.

Since typical heat guns are not designed to expel the heated air at such human tolerable air pressures that are regularly set in CPAP machines, there is a needed determination to make sure that the heated air, which is heated at a predetermined temperature comparable to cause apoptosis programmed cell death of the esophageal tumor, for example, or at sauna levels of 150° F. or above, is pumped into through a heat resistant-type tube (rated for high temperatures) and into the person's improved face mask disclosed in this application, at air pressure of no more than 11 Hg, or 5.4 psi at the upper level of human respiratory tolerance, or preferably a lower amount, such as for example, at 5.88 Hg or 2.88 psi.

For safe inhalation at human respiratory rates, the volume of air must be controlled down from the high rates capable of being expelled by a heat gun in industrial applications, down to an acceptable level tolerable by human respiration. For example, tidal volume (symbol VT or TV) is the typical human lung volume, representing the normal volume of air displaced between normal inhalation and exhalation when extra effort is not applied. In a healthy, young human adult, the tidal volume is approximately 500 mL per inspiration or 7 mL/kg of body mass. Furthermore, a normal minute volume, while resting, is about 5-8 liters per minute in humans. Minute volume generally decreases when at rest and increases with exercise. For example, during light activities, minute volume may be around 12 liters. Since heat guns are capable of producing heated air at about 190 liters per minute, the air volume can be titrated down to 5-8 liters per minute, or 12 liters per minute, or 50 liters per minute, whichever is best for the person being treated.

In the present invention, the prior art of Sabin '861 heat gun must have the capability of providing heated air in the range of 80° F. to 275° F., preferably at sauna heat temperature levels of about 113 degrees F. to about 140+ degrees F., and at constant air pressure levels of no more than about 5.4 psi for human respiratory tolerance. While any heat gun which is capable of the aforementioned temperature and air pressure range limitations, non-limiting examples of such heat guns include the Master Pro Heat Gun models 1400 and 1500

In the prior art of Sabin '861 Master heat gun model PH-1400, which operates at 120/230 V AC, outgoing air temperatures can be as low as 113 degrees F., extending up to 1000 degrees F. The Master heat gun model has a finger-operable ON/OFF switch on a trigger position of the handle, which has three setting depending upon selected movement of the switch. In a "HEAT" position, the top of the switch is depressed inward. To achieve a "COOL" position, the switch is set so that the top and bottom portions are equally extended. To turn the switch off, the bottom of the switch is completely pushed inward.

For use in provided heated air through a heat resistant flexible hose to a CPAP type face mask covering the nose and mouth of the person, the Master Pro Heat gun model PH-1400 can also be set at a human tolerable upper limit, such as for example 200F or even 300° F., if medically appropriate, at air flow volumes of as little as 4 CFM (cubic feet per minute). The rear of the heat gun handle has a pair of turnable knobs, where the left knob is twisted and turned to adjust the airflow up or down to predetermined human tolerable levels, which are displayed in an LCD screen above or adjacent to the knobs. To adjust the temperature of the emitted air, the right knob is twisted and turned to raise or lower the designated heat of the air flow output. A set temperature is displayed for several seconds, until the actual output air temperature is displayed on the LCD screen.

A further safety prior art of Sabin '861 feature in the Master Pro Heat gun model PH-1400 is that adjacent to the two knobs there is provided a locking lever or key, typically but not necessarily magnetic, that is pushed or moved to set and lock the output air temperature and pressure. The settings inputted by the two knobs cannot be changed if the LCD indicates a "Lock" icon, due to the manipulation of the locking lever or key. The locking lever or key can alternatively be used for converting the temperature from Fahrenheit units to Celsius.

Alternatively, the prior art of Sabin '861 Master heat gun model PH-1500, also operates at 120/230 V AC, outgoing air temperatures can be as low as 113 degrees F., extending up to 1000 degrees F. The Master heat gun model 1500 also has a finger-operable ON/OFF switch on a trigger position of the handle, which has three setting depending upon selected movement of the switch. In a "HEAT" position, the top of the switch is depressed inward. To achieve a "COOL" position, the switch is set so that the top and bottom portions are equally extended. To turn the switch off, the bottom of the switch is completely pushed inward.

For use in provided heated air through a heat resistant flexible hose to a disclosed herein face mask covering the nose and mouth of the person, the prior art of Sabin '861 Master Pro Heat gun model PH-1500 can also be set at a human tolerable upper limit, such as for example 200 F or even 300 F, if medically appropriate, at air flow volumes of as little as 4 CFM (cubic feet per minute). The rear of the heat gun handle also has an LCD screen, but adjacent to, or below, the LCD screen there is provided an array of programmable settings with keypad up/down arrow keys, where the left up and down arrow keys are manipulated to adjust air pressure and the right up and down arrow keys are manipulated to adjust the temperature up or down to predetermined human tolerable levels, which are displayed in an LCD screen above or adjacent to the key pad. In the middle between the left and right-side arrow keys are two other keys, where the upper key has a "P" inscribed thereon, for program the desired inputted air pressure and temperature outputs. The lower middle key is used to change the output levels from Fahrenheit to Celsius, or vice versa.

A further safety feature in the prior art of Sabin '861 Master Pro Heat gun model PH-1500 is the programmable keys can be used to set and lock the output air temperature and pressure. The settings inputted by the two knobs cannot be changed if locked by the programmable keys.

While other heat guns with the aforementioned locking capabilities can be used, another example is the Steinel pistol grip heat gun model HG 2520 E which can produce temperatures in the range of from as low as 120° F. up to 1300° F. (50 to 700° C.), which has pressures as low as from 2 to 13 CFM, and programmable safety override functions. Additionally, the Seekone Heat Gun 1800 W has a dial with variable temperature controls.

Another useful prior art of Sabin '861 heat gun for providing the elevated heat source is the Wagner 0503049 HT4500 Heat Gun, which has fifty-five temperature choices by button. The temperature of the outgoing air at the nozzle tip of the Wagner HT 4500 heat gun can be as low as 120° F. minimum. As the heated air travels through the flexible heat resistant hose, the temperature of the air is reduced at the beginning of the CPAP mask to about 130° F. The Wagner HT 4500 heat gun has an LCD screen at the back of the gun, with a pair of touch responsive keypad buttons for increasing or decreasing temperature, and another set of touch responsive keypad buttons for increasing or decreasing output air pressure.

In a further alternate embodiment, in a hospital setting, the prior art of Sabin '861 heat gun can be installed on a mobile I.V. stand, with more than one heat gun attached to an individual I.V. stand, or collapsible folding cart, with an AC wall outlet or, optionally, to a Honda generator on the cart for full ambulatory use (when in ventilated conditions to eliminate carbon monoxide), which lasts over eight hours at ¼ power. It can last over three hours at full power, and by dividing the pressurized heated air, can treat two people with one machine. For example, the conversion of CFM to liters per minute is 28.32; thus, a heat gun at 120° F. heat at 3.5 CFM times the factor of 28.32=99.12 liters per minute. Since a human takes 5-8 liters at rest, therefore the present invention can bleed off 99.12 minus 8=91.12 liters per minute, for treating in two persons simultaneously.

While the aforementioned prior art of Sabin '861 heat guns require 120V AC power to operate other cordless heat guns with rechargeable batteries can also be utilized to provide controlled hear and air pressure suitable for human respiration, with air pressure reduction controls, so that the pumped air is limited to the human tolerable air pressures of about no more than about 5.4 psi. An example of a cordless heat gun that can run up to 42 minutes between recharging the battery is the DeWalt 20V Max Cordless Heat Gun. Another cordless heat gun is the Ryobi cordless 18V heat gun has a concentrated heated air flow typically used for electronic board repair applications such as shrinking shrink tubing for insulating cable ends, or at high temperature removing defective modules by melting solder at the contact tabs. It is powered by a 3 Ah 18v battery that weighs 1.72 pounds (and stores 54 Wh worth of energy).

As described in the prior art of Sabin '861, for further safety control, anti-microbial or stainless-steel hygienic ball valves can be deployed in the flexible heat resistant tubing, between the heat gun heat source and the CPAP-type face mask. A first ball valve may be deployed as a "T" configuration, such as an Eldon James Antimicrobial high density polyethylene (HDPE) threaded tee, in line with the heat gun output nozzle and the hose of a flexible polymer tubing, such as, TYGON 3350 or TYGON 54297. The hygienic ball valve, which is preferably is one of ¾ full port SS 2-pc. ball valves, is connected at the "T" with a hose coming off of it, functioning as a pressure bleed valve. A second hygienic ball valve is a resister valve deployed near the mask, which, as a restrictor valve, restricts air from the gun traveling into the mask if it exceeds medically acceptable values. Manipulation of these two valves achieves the desired airflow and heated temperature of the air being delivered from the heat gun to the person, through the CPAP-type mask.

As described in the prior art of Sabin '861, Other optional safety controls include air pressure controllers, to keep the heated air at those lower levels of pumped air pressure, compatible to what are used conventionally in CPAP machines, so that the incoming heated air flow is also limited to "human tolerable air pressure", which typically may be no more than about at 15 cm/H20, or 11 Hg, or 5.4 psi, or within the CPAP acceptable range of air pressure of 6 to 15 cm/H20, or 4.4 Hg to 11 Hg, or 2.16 psi to 5.4 psi.

As described in the prior art of Sabin '861, for those low human tolerable air pressure flows, optionally there may be provided a microprocessor-controlled air pressure distributor associated with the heat gun, so that the psi of the outgoing air pressure can be maintained at those low human tolerable air pressures, regardless of the heat of the air.

In general, since the device is a medical device, optimally the prior art of Sabin '861 heat guns have air temperature and air pressure controls, such as thermostats for temperature control, with automatic shutoff features and interlock. For example, the Master Pro Heat gun has a minimal CFM of 4 and a safety interlock built-in for temperature and air flow stopping. Converted to liters=0.28 Liters per minute, this is below the air flow of a human at rest with normal activities, which is about 5-8 liters per minute.

In connection therewith, while the prior art of Sabin '861 heat guns may have finger operable keys for controlling air temperature and air pressure, optionally these person operable controls and shutoffs may also have a simple AC wall outlet plug-in adapter that acts as a fail-safe automatic shutoff and interlock preventing any heat output above a threshold maximum and preventing any air pressure above a threshold maximum, such as tolerated in a CPAP machine, to prevent accidental increases of temperatures and air pressures above what is tolerable in human respiration.

Since a heat gun is a powerful device plugged into potentially lethal voltage and can deliver powerful airflow and temperatures to 1000° F., Applicant has tested temperatures at the tip of the heated air output, at a distance of one inch out therefrom, of the heat gun when on full heat, in replicate six+ times. When the heat gun claims to emit heated air at 1200° F., Applicant measured the actual heated air from the heat gun to be about 487° F. Therefore, the listed manufacturing of heat guns' base temperature on the red-hot nozzle tip at a distance of about two inches from the tip of the heat gun is widely exaggerated. However, it may be desirable in certain environments to use a safety interlock AC outlet plug-in adapter, to separately monitor the temperature and pressure delivered to a patient and to shut down the system in case either the pressure or temperature in the patient hose exceed predetermined safety limits of heated air and pressure, tolerable in human respiration.

In general, as described in the prior art of Sabin '861, in case of shut down, manual intervention (physically pressing the start button) is often required. Since the safety interlock plug-in adapter is plugged into the wall outlet and the heat gun is plugged into the adapter (like plugging three prong plugs into two prong wall outlet adapters), the heat gun need not be modified, but an extra degree of safety would be gained by changing the plug or line cord and plug of the heat gun to one with a keyed plug that no longer fits a wall plug. A mating outlet on the safety plug-in adapter would fit the keyed plug of the heat gun.

Such a simple prior art of Sabin '861 interlock adapter that is plugged into an AC outlet between the AC outlet and the AC compatible plug of the heat gun typically includes an AC relay, with normally open single pole contacts. An AC coil and related contacts make up a simple relay, which has separate ON and OFF momentary switches. One switch has normally open contacts and the other switch is in the relay latching circuit and it has normally closed contacts. A thermal sensor switch with normally closed contacts is selected from a factory list of available temperatures. The maximum temperature selected must be above the range of operating temperatures. A normally closed pressure sensing switch interfaces with the airflow to sense a pressure beyond operating region that is close to being a safety hazard. A fuse can complete the circuit.

As also described in the prior art of Sabin '861, the aforementioned simple interlock plug-in adapter is a fail-safe shutoff to completely shut the heat gun down if the heat gun itself has a malfunction in its operation or use.

BRIEF DESCRIPTION OF THE DRAWINGS

The present invention can best be understood in connection with the accompanying drawings, it is noted that the invention is not limited to the precise embodiments shown in the following drawings, in which:

FIG. 1 is a perspective view of a healthcare provider administering heated air to a lesion on the skin of a patient, where the temperature of the heat equals the temperature of the skin lesion being treated, not the temperature of the heat exiting from the heat gun.

FIG. 2 is a close-up detailed view of the LCD viewing screen, taken along dashed view circle line "2" of FIG. 1, showing the temperature of the exiting air from the heat gun through a nozzle pointed at the skin lesion.

FIG. 3 also shows a plurality of templates of varying area sizes, fitting to different sized skin lesions, whereby the area of the skin outside of the lesion is protected from direct contact with the exiting heat from the heat gun.

FIG. 3a is a close-up detailed view of a clamp holding a masking template shown in FIG. 3, at the distal end of the clamp, whereby the proximal end (not shown) includes a rod handle for manual or stationary holding of the clamp and masking template.

FIG. 5 also shows the healthcare practitioner holding the heat gun and a medical assistant holding a separate handheld non-contact surface temperature measuring device.

Figure 3:
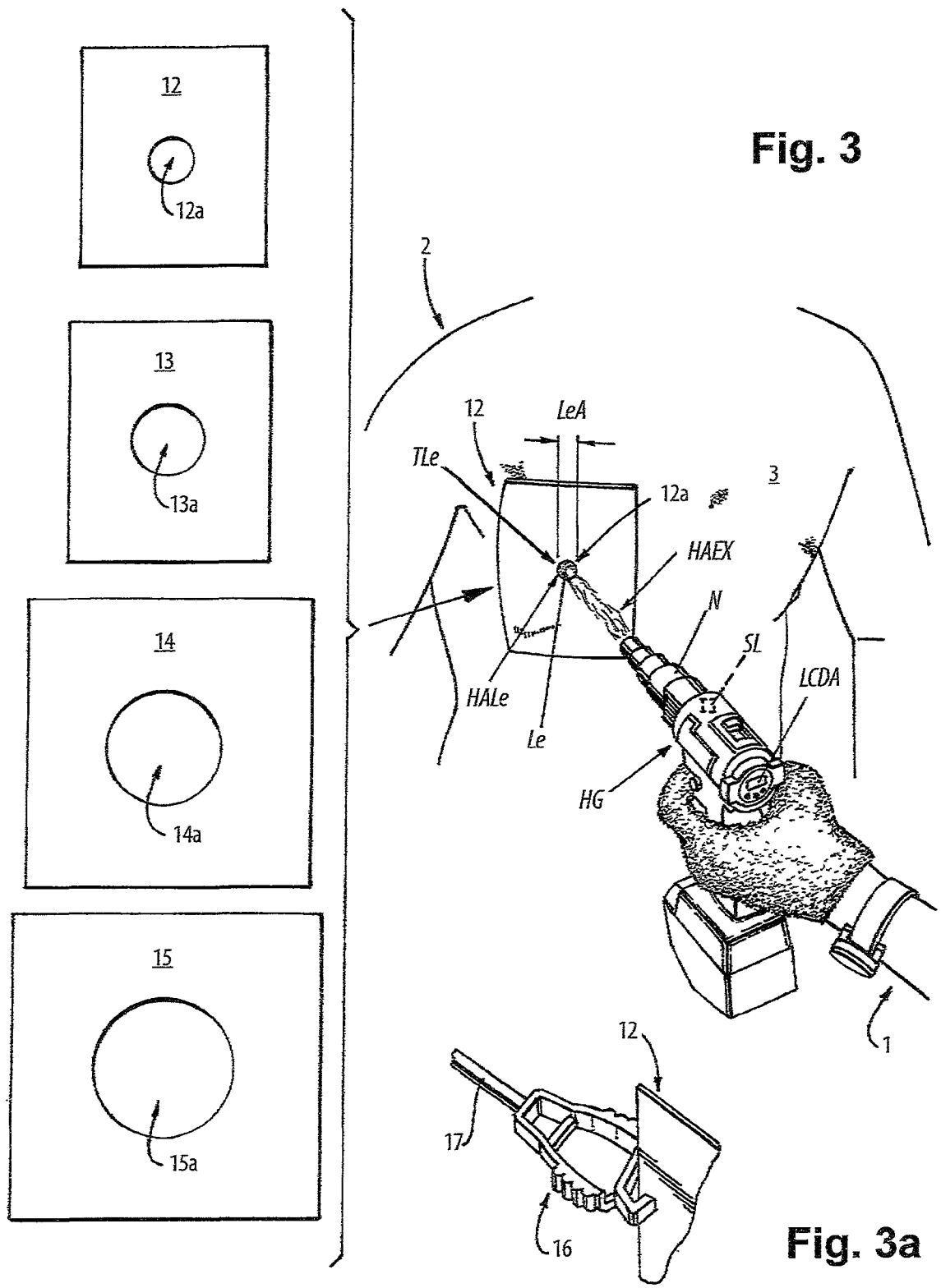
FIG. 3 is a front perspective view, as in FIG. 1, showing the healthcare provider administering heated air to a lesion on the skin of a patient, where the heat is limited to the area of a hole on a masking template, and the hole is configured to be limited to the area of the skin lesion.

The heat from the heater air inspiration through the trachea migrates/transmits/disperses across the membrane separating the Trachea/windpipe from the esophagus and hits the esophagus with heat.

DETAILED DESCRIPTION OF THE INVENTION

The present invention has broad applications to many medical fields for a variety of therapeutic applications. However, it is particularly adapted for patients afflicted with skin afflicted lesions caused by pathogens. The drawings are for illustrative purposes only, and the preferred mode for carrying out the invention is described herein.

As used throughout this specification, the word "may" is used in a permissive sense (i.e., meaning having the potential to, or being optional), rather than a mandatory sense (i.e., meaning must), as more than one embodiment of the invention may be disclosed herein. Similarly, the words "include," "including," and "includes" mean including but not limited to.

The phrases "at least one," "one or more," and "and/or" may be open-ended expressions that are both conjunctive and disjunctive in operation. For example, each of the expressions "at least one of A, B and C", "one or more of A, B, and C", and "A, B, and/or C" herein means all of the following possible combinations: A alone; or B alone; or C alone; or A and B together; or A and C together; or B and C together; or A, B and C together.

Also, the disclosures of all patents, published patent applications, and non-patent literature cited within this document are incorporated herein in their entirety by reference. However, it is noted that the citing of any reference within this disclosure, i.e., any patents, published patent applications, and non-patent literature, is not an admission regarding a determination as to its availability as prior art with respect to the herein disclosed and claimed apparatus/method. Furthermore, any reference made throughout this specification to "one embodiment" or "an embodiment" means that a particular feature or characteristic described in connection therewith is included in at least that one particular embodiment. Thus, the appearances of the phrases "in one embodiment" or "in an embodiment" in various places throughout this specification are not necessarily all referring to the same embodiment. Therefore, the described features, advantages, and characteristics of any particular aspect of an embodiment disclosed herein may be combined in any suitable manner with any of the other embodiments disclosed herein.

In connection with the present invention, the drawings show one or more embodiments, but the present invention is not limited to that shown in the drawings, in which FIG. 1 shows a healthcare provider 1 administering heated air flow HAF from heat gun HG at a first exiting temperature HAEX toward a lesion Le on the skin 3 of a patient 2, for a time period of about thirty (30) seconds, whereby in the thirty (30) second time duration, the higher temperature HAEX of the heated airflow HAF is slightly cooled down to a temperature TLe of the skin lesion Le being treated. Therefore, the reduced temperature TLe at the site of the skin lesion Le, is the actual temperature required to inactivate the pathogen causing the skin lesion Le, not the initial exiting temperature HAEX of the heated exiting air, exiting from the heat gun HG. A typical heat gun HG can be a Milwaukee cordless portable heat gun with an 18V battery, with assorted nozzles N. Optionally the heat gun can be corded to an AC outlet at 120V AC power. The heat gun HG also has built-in safety locks SL, such as disclosed in Applicant's U.S. Pat. No. 11,234,861 B2, issued Feb. 1, 2022, and Applicant's U.S. Pat. No. 10,905,585 B1, issued Feb. 2, 2021, to control the exiting heated air temperature HAEX to a predetermined lockable safe temperature for topical application to the skin 3 of a patent 2, and/or where the heat gun is shutoff when a predetermined safe threshold temperature to the skin 3 of a patient 2 is reached.

For example, FIG. 1 also shows the heat gun HG, having safety locks SL provided therewith, where the nozzle N provides heated air at about 120 to about 130° F. from the concentrated heat source (heat gun HG) through a short tube to the nozzle N for destroying pathogens causing lesions Le in extensive blotches on and under the skin of the patient shown in FIG. 1, such as, for example, from Leishmaniasis pathogens, i.e. protozoa causing cutaneous Leishmaniasis, or other viral and/or idiopathic pathogens causing skin cancers, abnormal pre-cancer dysplasia cells, and which destroy other diseases and pathogens on the skin.

Figure 5:
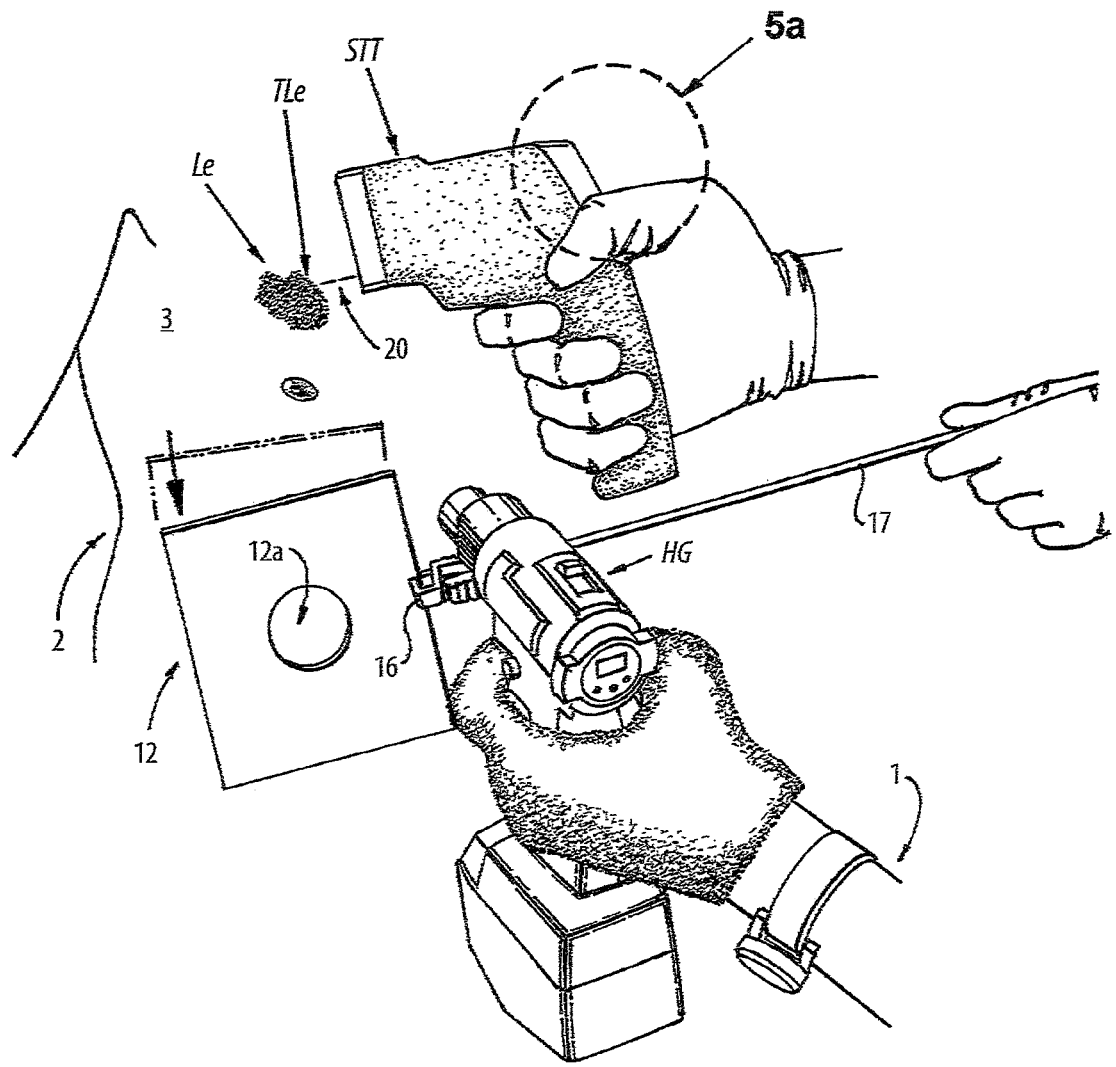
FIG. 5 is a local perspective view, showing the practitioner's hands holding an alternate embodiment for a heat gun, used in connection with a separate handheld non-contact surface temperature measuring device, which remotely measures the actual skin temperature threshold of the skin lesion in situ being measured by a laser infrared light beam, and where the skin lesion is treated by hot air exiting the heat gun at a temperature which renders the skin temperature threshold to be effective in treating the skin lesion.
Figure 5A:
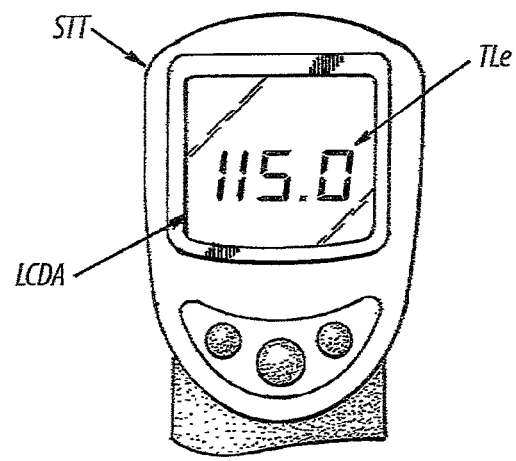
FIG. 5A is a close-up detailed view of the alternate embodiment of the separate handheld non-contact surface temperature measuring device, taken along dashed view circle line "5a" of FIG. 5, with a single LCD viewing screen, displaying the threshold temperature of the skin lesion being treated.

FIG. 1 also shows a typical heat gun HG, which can have temperature control locks and interlocks SL (such as explicitly disclosed in Applicant's '861 patent and '585 patent, incorporated by reference herein, in its entirety), to keep the outflowing hot air HAEX to cool down to the therapeutic temperature TLe of the skin being treated of about 105° F.-180° F., optionally, in a range of 105° F.-135° F., preferably at about 120° F. to about 130° F. While the LCDA of the heat gun HG displays the programmed temperature of the heated air flow HAF required to achieve the actual required temperature TLe of the skin lesion Le on the skin 3 of a patient 2, to inactivate the pathogen causing the skin lesion Le, can be accurately measured by using a remote portable handheld contactless surface temperature device STT aimed at the actual surface of lesion Le being treated on the skin 3 of the patient 2. Such remote portable handheld contactless surface temperature devices are shown in FIGS. 5 and 5a, such as, for example, manufactured by Berrcom or other similar thermometers using laser infrared signal focused on the skin lesion Le being treated, so that the heat gun can be shut off when the threshold skin lesion temperature TLe is reached, to inactivate and destroy the pathogen which caused the skin lesion to erupt on the skin 3 of a patient 2.

FIG. 2 shows the LCD viewing screen LCDA of heat gun HG, showing the temperature TAEX of the exiting air flow HAF, from the heat gun HG through a nozzle N, pointed at the skin lesion Le on the skin 3 of the patient 2. The LCD viewing screen LCDA displays the temperature of the heat HAEX exiting from the heat gun HG.

FIG. 3 shows the healthcare provider 1 administering heated air HALe to a lesion Le on the skin 3 of a patient 2, where the heat HALe is limited to the area/diameter of a hole 12a on a masking template 12. The hole 12a is configured to be limited to the diameter area LeA of the skin lesion Le. FIG. 3 also shows a plurality of masking templates 12, 13, 14, 15, each having respective holes 12a, 13a, 14a, 15a of varying area sizes, fitting to different sized skin lesions Le, whereby the area of the skin 3 outside of the lesion Le is protected from direct contact with the exiting heat HAEX from the heat gun HG through the nozzle N, before it arrives as heated air HALe, at the preferred temperature TLe of the skin lesion Le, capable of inactivating and destroying the pathogen causing the lesion Le on the skin 3 of a patient 2 afflicted with Cutaneous Leishmaniasis or other skin lesion causing diseases.

FIG. 3a shows clamp 16 holding a masking template 12 of FIG. 3, at the distal end of the clamp 16, and whereby the proximal end (not shown) includes a rod handle 17 for manual or stationary holding of the clamp 16 grasping masking template 12 with hole 12a, while the heat gun HG sends heated air HAEX toward the skin lesion Le, protecting adjacent skin 3 without a lesion Le, by optional masking template 12 with a hole 12a exposing only the skin lesion Le therethrough.

Figure 4:
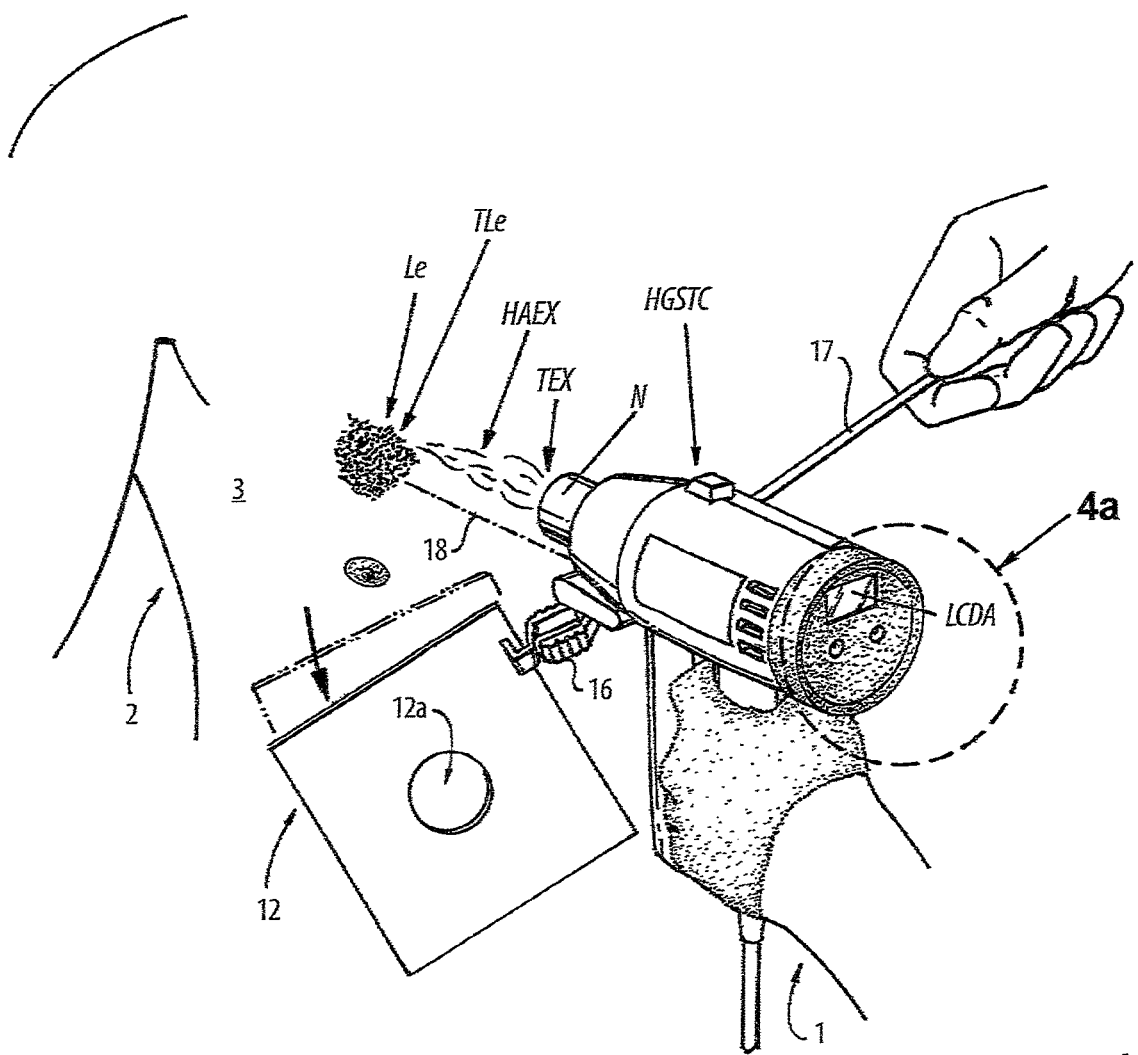
FIG. 4 is a local perspective view, showing the practitioner's hands holding a preferred embodiment for a heat gun, having a built in non-contact surface temperature control (STC), which remotely measures the actual skin temperature threshold of the skin lesion in situ being measured by a laser infrared light beam in real time, and where the skin lesion is treated by hot air exiting the heat gun at a temperature which renders the skin temperature threshold to be effective in treating the skin lesion.

FIG. 4 shows the practitioner 1's hands holding a preferred embodiment for a heat gun HG-STC, having a built in non-contact surface temperature control (STC) operating via laser infrared light beams 18, which remotely measure the actual skin temperature threshold TLe of the skin lesion Le in situ, being measured by the laser infrared light beam 18. preferably in real time (but not required), and where the skin lesion Le is treated by hot air HAEX exiting the heat gun HG-STC, but which, after incidental cooling through the air from the nozzle N of the heat gun HG-STC, arrives at the skin lesion Le at a lowered threshold temperature TLe. The skin threshold temperature, measured remotely by the laser infrared light beams projected on the surface of the skin lesion Le threshold at the skin lesion Le, is effective in treating the skin lesion Le, by inactivating and destroying any pathogen causing the skin lesion Le to proliferate upon the skin 3 of the patient 2. The important threshold temperature TLe is the heated air temperature at the exact location of the skin lesion Le, that renders and inactivates the pathogen causing the lesion Le on the skin 3 of the patient 2.

FIG. 4 also shows a masking template 12 having a hole 12a exposing only the skin lesion Le being treated, where the masking template isolates the unaffected skin 3 of the patient 2 being treated, from heated air from heat gun HG STC, having a built-in non-contact temperature sensing device STT, with an LCD screen LCD-STC, displaying both the temperature the heat gun HG-STC (i.e. shown as 120 degrees F. in FIG. 4a), and temperature Tle at the lesion Le (i.e. shown as 120 degree F.). When the lesion Le is exposed to the threshold temperature TLe, the lesion-activating pathogen is inactivated and destroyed by exposure to the hot air measured as TLe at the lesion Le upon the skin 3 of the patient 2. Such a heat gun HG STC may be a Master Pro-Air STC heat gun corded to 120V AC power. The Master Pro-Air STC is the only currently available Surface Temperature control heat gun in the world. The Master Pro-Air STC is also capable of delivering the heated air flow at air pressures of from about 4 cubic feet per minute (i.e., CFM) to about 8 CFM, or more, up to 16 CFM, as determined the patient's health care practitioner.

While not having a built-in laser infrared thermometer, the programmable Master ProHeat 1400A Digital Professional model can be used in conjunction with a remote handheld non-contact thermometer.

Figure 4A:
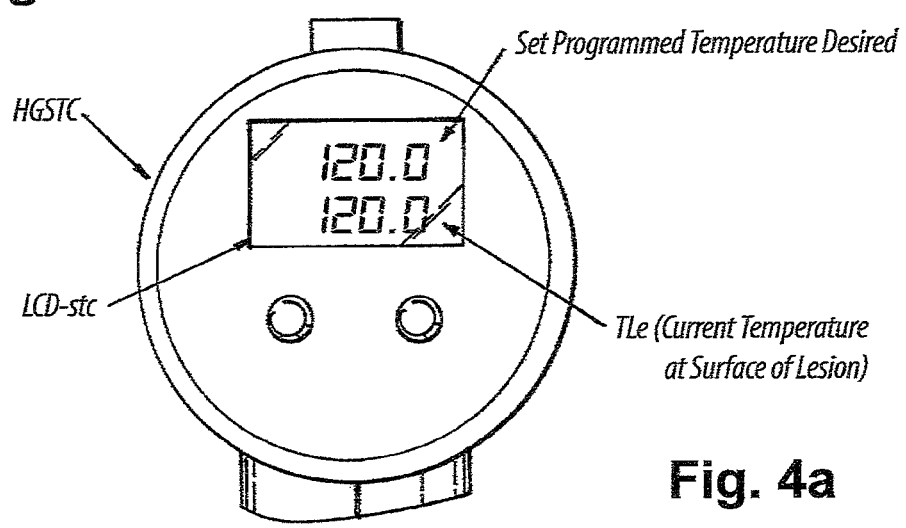
FIG. 4A is a close-up detailed view of the preferred embodiment for a heat gun with a dual LCD viewing screen, taken along dashed view circle line "4a" of FIG. 4, displaying both the target surface temperature selected on the top of the LCD screen, and below, the current moving threshold temperature of the surface being treated on the bottom of the LCD screen.

FIG. 4A shows the preferred embodiment for a heat gun HG-STC with a dual LCD viewing screen LCD-STC, displaying the programmed selected surface temperature on the top of the LCD-STC screen, (i.e. 120 degrees F.), in order to achieve the desired threshold temperature TLe (i.e. 120 degrees F.) of the skin lesion Le being treated, displayed on the bottom of LCD screen LCD-STC.

With respect to use and operation of the Master ProAir STC (identified herein as HG-STC), with a built-in contactless laser infrared temperature thermometer, Applicant incorporates by reference in its entirety, the Instruction Manual thereof, submitted in the Information Disclosure Statement (IDS) filed herein, which discusses the simultaneous use of the heat gun with its built-in contactless temperature thermometer for measuring surface temperatures (being used herein to measure the threshold temperature TLe of the skin lesion being treated, by inactivating and destroying the pathogen which caused the proliferation of the skin lesion Le). The Instructional Manual also discusses choice of nozzles, using a trigger switch and trigger lock, how to operate the gun pressing the trigger switch for the heating element and fan startup, aiming the laser infrared light beams at the target to be measured upon heat application thereto, engaging and releasing the trigger lock, using the PROLOC supervisory key to change between supplying heated air and measuring surface temperature at the lesion Le, and using the surface temperature controls, along with explanatory diagrams associated therewith.

FIG. 5 shows the practitioner 1's hands holding an alternate embodiment for a heat gun HG, used in connection with a separate handheld non-contact surface temperature measuring device STT, which remotely measures the actual skin temperature threshold TLe of the skin lesion Le in situ, being measured by a laser infrared light beam 20 (as shown in FIG. 5a), and where the skin lesion Le is treated by hot air HAEX exiting the heat gun HG and reduced by airflow to a lower threshold temperature TLe at the site of the skin lesion Le, which lower threshold temperature renders the skin temperature threshold TLe to be effective in treating the skin lesion Le. FIG. 5 also shows the healthcare practitioner 1 holding the heat gun HG and a medical assistant holding the separate handheld non-contact surface temperature measuring device STT.

FIG. 5A shows the alternate embodiment of the separate handheld non-contact surface temperature measuring device STT, as in FIG. 5, with a single LCD viewing screen LCDA, displaying the threshold temperature TLe (i.e. 115 degrees F.) at the skin lesion Le being treated.

When administering inhaled heat through the trachea of a patient, the temperature of the esophageal tumor being treated by heat conduction through the thin tracheoesophageal party wall sheath membrane, can be measured via hand held devices, such as ultrasound transducers, in a similar manner to the hand held temperature monitors shown in FIG. 5A, for measuring skin surface temperature, where the temperature data can be displayed in real time during administration of the inhaled heated air, such s disclosed in Raiko et al, in Imaging based internal body temperature measurements, in the Journal of "temp-toolbox" in TEMPERATURE, Vol 7, no. 4 at KTMP 71769006, discloses non-invasive temperature measurements of internal body tissues.

Figure 6:
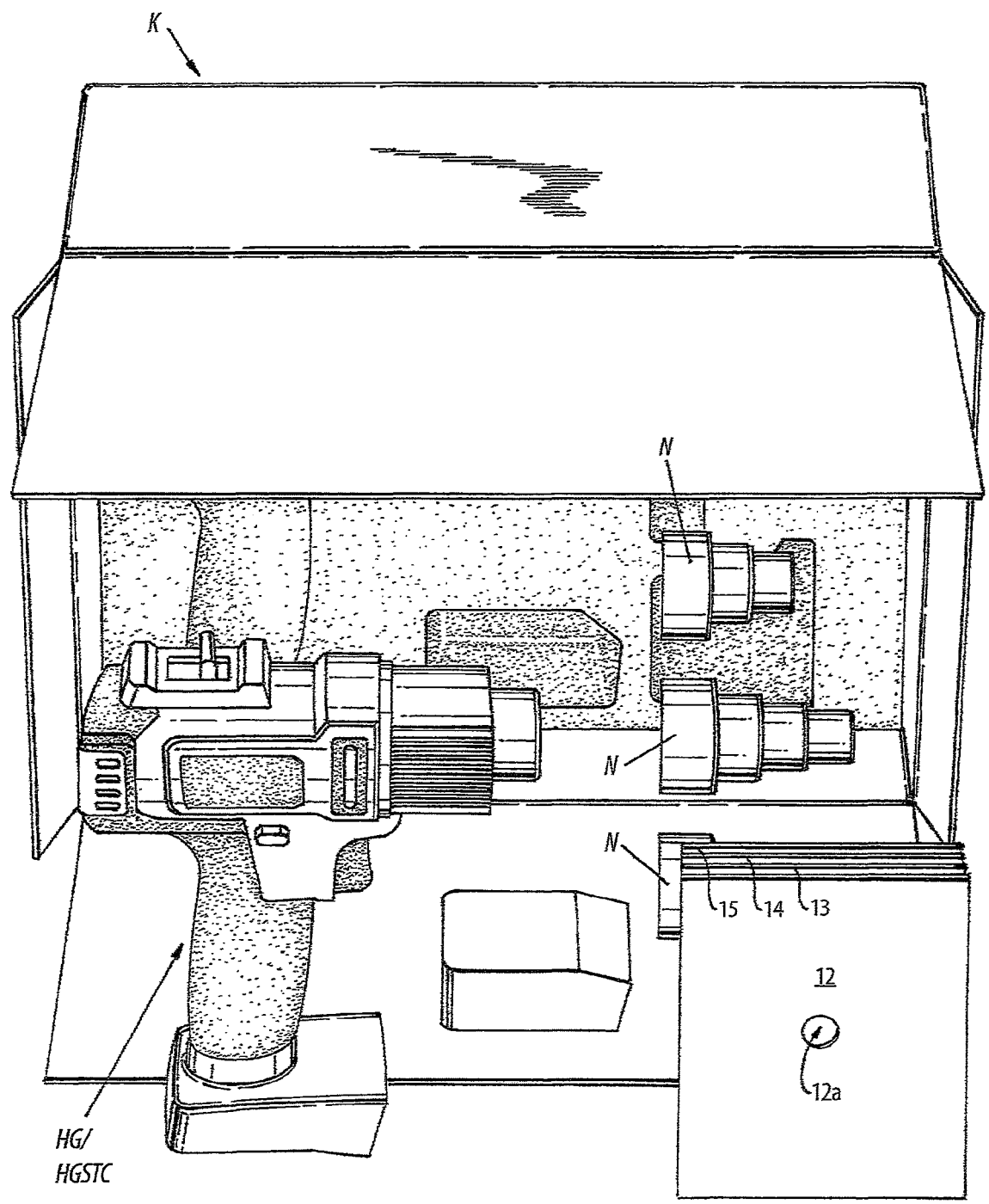
FIG. 6 is a front perspective view of the heat gun of FIG. 1 or 3, provided with a set of nozzles of varying exiting diameters, and a set of masking templates with a set of varying area sizes, fitting to different sized skin lesions.

FIG. 6 shows the heat gun HG or HGSTC of FIG. 1 or 3, provided in a kit K, with a set of nozzles N of varying exiting diameters, and a set of masking templates 12, 13, 14, 15 with a set of varying area hole sizes 12a, 13a, 14a, 15a, fitting to different sized skin lesions Le. If the heat gun HG does not have a remote contactless thermometer, then the kit can be used with a handheld surface thermometer STT, shown in FIG. 5.

Figure 7:
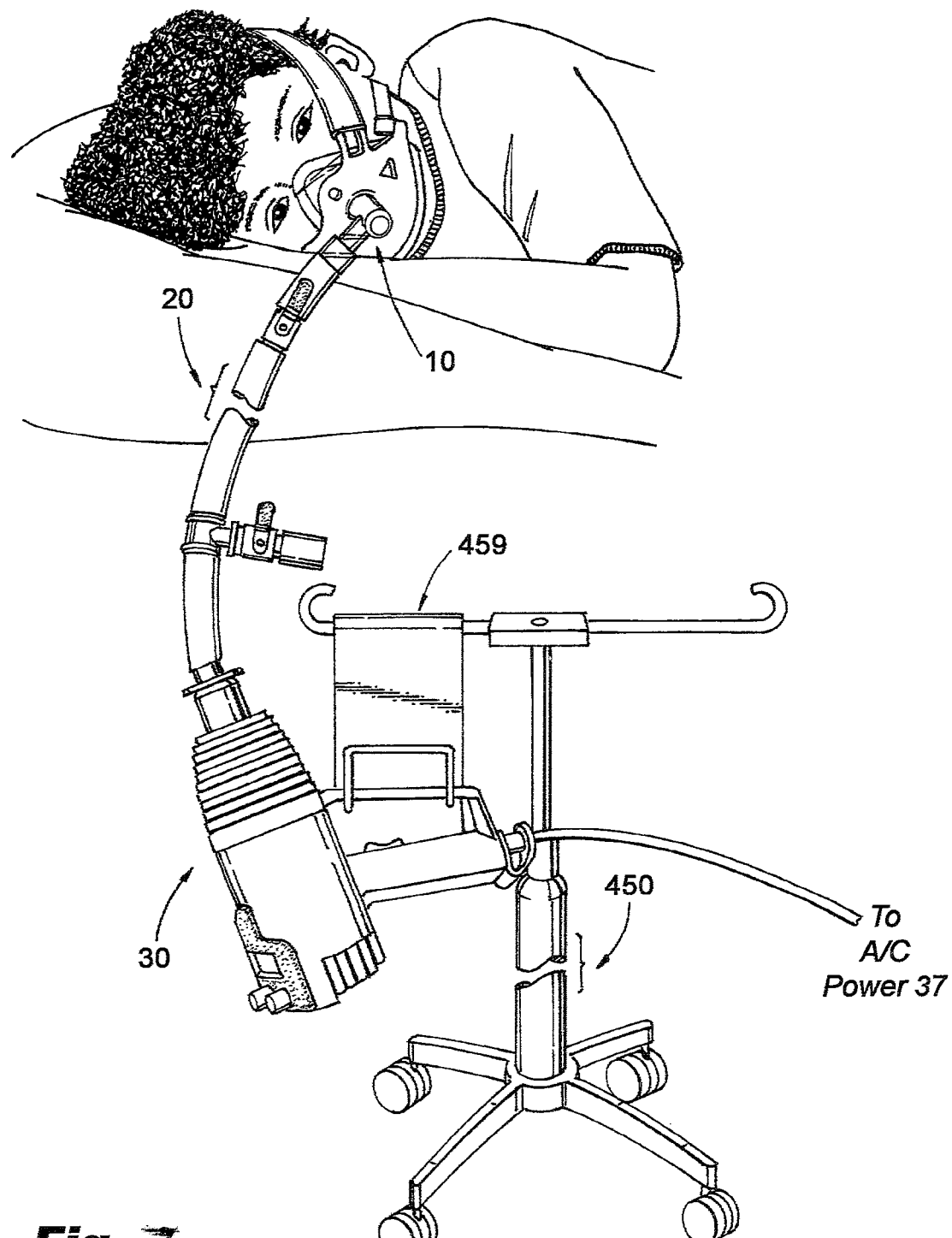
FIG. 7 is a perspective view of a prior art of Sabin '861 inhalation delivery of heated air for treatment of respiratory illnesses.

FIG. 7 shows a prior art of Sabin '861 describing inhalation delivery of heated air for treatment of respiratory illnesses.

Figure 8:
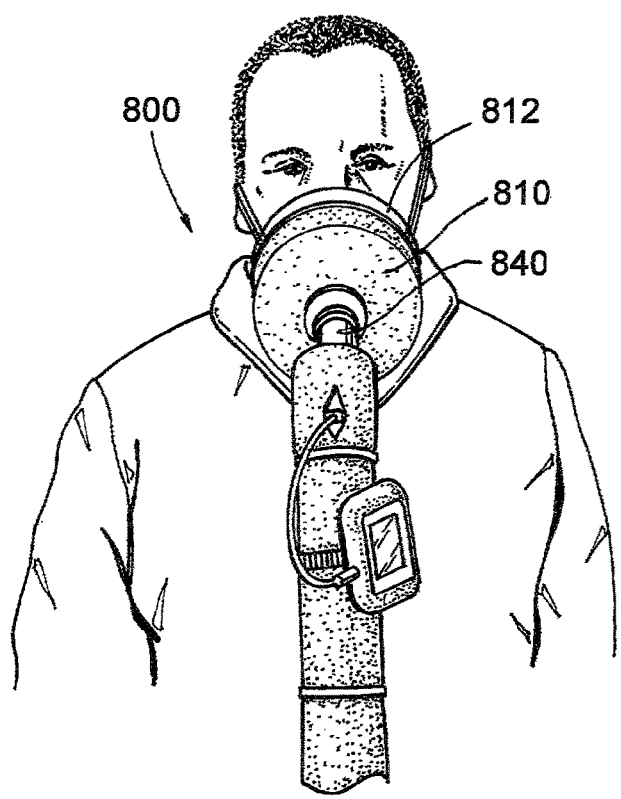
FIG. 8 is a front-perspective view of an alternate embodiment for a prior art of Sabin '861 inhalation delivery of heated air for treatment of respiratory illnesses.

FIG. 8 shows an alternate embodiment for the prior art of Sabin '861 inhalation delivery of heated air for treatment of respiratory illnesses.

Figure 9:
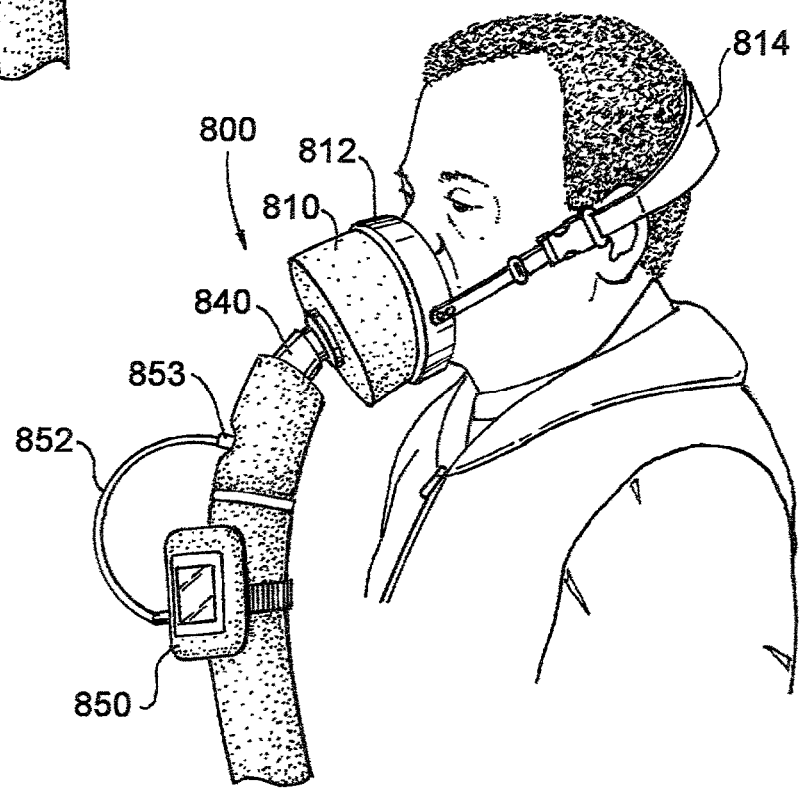
FIG. 9 is a side-perspective view of the prior art of Sabin '861 inhalation delivery of heated air for treatment of respiratory illnesses, as in FIG. 8.

FIG. 9 shows the prior art of Sabin '861 inhalation delivery of heated air for treatment of respiratory illnesses, as in FIG. 8.

Figure 10:
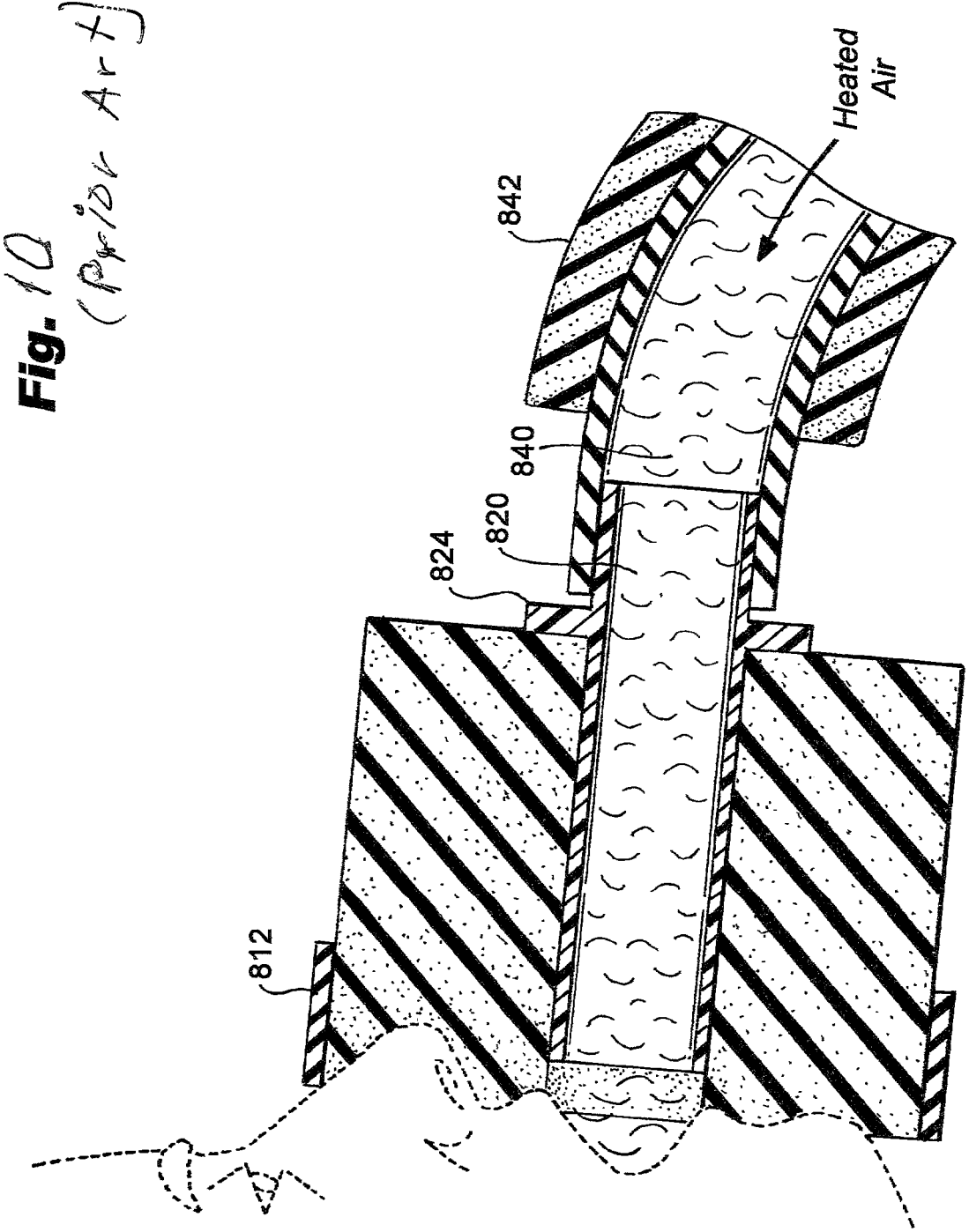
FIG. 10 is a cross-sectional cutaway view of the prior art of Sabin '861 inhalation mask for delivery of heated air for treatment of respiratory illnesses, showing heated air flow through the mouth of a patient.

FIG. 10 shows the prior art of Sabin '861 inhalation mask for delivery of heated air for treatment of respiratory illnesses, showing heated air flow through the mouth of a patient. FIG. 10 is a detail cross sectional view showing the attachment of the prior art of Sabin '861 semi-rigid silicone tube extending through the foam barrier, which has a distal heated air discharge end and a proximal end joinable via a joint to the insulated flexible conduit, which is connected to the heat source. The patient's lips interface with the foam barrier at the distal end of the rigid silicone tube. The opening in the foam barrier of the prior art of Sabin '861 device shown in FIG. 10 matches the matches the opening of the orifice of the ½ inch to about ¾ inch outer diameter (OD) sized silicone tube, while the lips interface with the foam, so that the heated air traffics from the hollow inside ½ inch internal diameter (id) orifice of the tubing, flowing directly to the open orifice of the user's mouth, so that the heated air is totally bypassing direct contact with the lips, nose and face of the user.

Not shown in prior art of Sabin '861 FIG. 10 is a detachable manometer or CPAP-type gauge to measure air pressure, which quick connects to the opening where the tubing exits the foam. Preferably, the face mask heats air to a sufficiently high temperature is between about at least 80 OF and about 275° F., optionally, which the sufficiently high temperature is at least 132.8° F. at a relative humidity of from about 90% to about 95% relative humidity.

In order to keep the pressure of the heated air at a tolerable level compatible with human respiration, the air pressure of the heated air is compatible with typical air pressure flows in a Continuous Positive Air Pressure (CPAP) machine. Most CPAP machines pump air in the range from 6 to 15 cm/H2O (centimeters of water pressure), such as, for example, an air flow is set at 8 cm/H2O.

In the present invention, the prior art of Sabin '861 heat gun 30, 130 or 530 must have the capability of providing heated air in the range of 113 degrees F. to 140 degrees F., preferably at sauna heat temperature levels of about 150 to 200° F. up to about 230° F., and at air pressure levels of no more than about 5.4 psi for human respiratory tolerance. While any heat gun which is capable of the aforementioned temperature and air pressure range limitations, non-limiting examples of such heat guns include the Master Pro Heat Gun models 1400 and 1500.

In the preferred alternate embodiment shown in in prior art of Sabin '861, at FIGS. 7-10, the face mask 800 includes a resilient, compressible barrier 810, made of polyurethane foam or other resilient compressible material, to provide a barrier between the mouth of the user inhaling hot air from heat.

While heat at approximately 130° F. can be tolerated by the lips of the user's mouth, but when the heat is raised to about 160° F. or above, the lips, face and/or eyes of the user can be injured, parched, or scorched from direct contact with the heated air.

However, when the prior art of Sabin '861 barrier 810 is provided in the form of a cylinder of foam of between 2 and 4 inches depth, preferably about 3 inches in depth, that depth provided isolates the lips from direct contact with the heated air, but permits the heated air to flow directly into the open mouth of the user, and directly into the respiratory system, without reducing efficacy.

To hold the prior art of Sabin '861 mask 810 with the compressible, resilient barrier 810, the barrier 810 is held in place in a collar 812 attached to head gear 814, which wraps around the skull of the user. The heated air from the heat source 838 trends through flexible conduit tubing 840, which is wrapped within an insulated sleeve 842. A temperature gauge 850 includes a sensor 853 piercing the flexible conduit 840 near the connection between the piercing the flexible conduit 840 near the connection between the silicone rubber tubing 820 within the barrier 810, where a cable 852 transmits the temperature detected by the sensor 853 to the thermometer 850 attachable to the insulating sleeve 842 of the heated air conduit 840. The thermometer 850 is also a Wi-Fi transmitter to a receiver, which has a safety beeping and flashing if set temperature is exceeded. An example of a thermometer is ThermoPro TP-07cooking thermometer. Semi rigid straight silicon tubing 820 is preferable 2-4 inches in length with an outer diameter of between ¾ inch and one inch, with ½ inch internal diameter (id) is ideal diameter. A quick release optional CPAP air pressure gauge can be provided to attach to the opening of the tube or/and a detachable manometer can also be used. The straight silicon tubing 820 is provided with joint shoulder collar 824, to facilitate connection to a flexible conduit tubing 840 from the heat source 838.

Therefore, the prior art of Sabin '861 heat mask 800 with the foam barrier 810 is a new, heat resistant soft barrier mouthpiece, as depicted in FIGS. 7-10, with a ½ inch internal diameter (id) heat emitting orifice of the tubing matching the open mouth of the patient, bypassing the lips, face, eyes, nose, cheeks, etc.

The prior art of Sabin '861 soft barrier mouthpiece mask 800, includes a cylindrical, face-conforming barrier block 810 of polyurethane foam (or optionally viscoelastic foam), which has more or less a ⅝ inch through-hole, in which the silicone tube 820 is attached proximally to the flexible hole 811, within block 810, and attached to conduit 840, connected to the heat gun heat source.

Moreover, the depth of the prior art of Sabin '861 foam cylindrical tubing 820 is 2 to 4 inches, preferably about 3 inches and the barrier cylinder block 810 has a diameter of about 5 inches, more or less.

Because the hot air comes out of the flexible tube 840 from heat source 838, and then goes through the straight silicone tube 820 therewithin, the user's lips are spaced apart from the exiting hot air of 175-180° F., coming from the flexible conduit 840 attached to the heat source 838, and the heated air is advanced through the straight silicone tubing 820 within the foam barrier cylindrical sleeve 810, directly into the respiratory airway and lungs of the user, while bypassing the FACE, lips of the user, because the lips surround the exterior circumference of the distal end of the straight silicone tubing 820, and the lips are not directly exposed to the hot air passing through the straight silicone tube 820, as the hot air is directed into the mouth orifice of the respiratory system.

A wearable strap assembly 812, 814 is provided with the cylindrical foam barrier 810 of the mask/mouthpiece 800, so that it stays comfortably on the face and skull of the wearer.

The prior art of Sabin '861 straight silicone tubing 820 is, for example, a Tygon 3355-1 Silicone tubing ½' inner diameter (id) and ¾' outer diameter (OD), with a ⅛' thick wall, heat resistant to 400° F., or other suitable tubing.

In the exploded view of prior art FIG. 10 of Sabin '861, the distal nozzle of heat gun 838 mates in a joint 832, including a nipple 834, wherein the nozzle of heat gun 838 is insertable within the nipple 834, which engages the open proximal end 836 of flexible tubing 840. At its opposite distal end, the flexible tubing 840 is connected to, and insertable within, the inner diameter of the proximal end of straight silicon tubing 820, extending within foam barrier 810 of mask 800, shown in FIGS. 8 and 9.

The heat source 838 contains internal and/or inline safety interlocks to monitor the temperature and the pressure of the heated and pressurized air delivered to a patient and to shut down the heat source 838 if the air temperature or the pressure of the air to be delivered to the patient exceeds preselected safety limits. For example, if one or more the predetermined safety limits is exceeded, a switch operates, so that the heat gun will not operate and a visual display with display indicates an "OFF" mode. The interlock may also include a mechanism for locking in a preferred predetermined temperature and pressure range capable of inactivating the virus causing COVID-19 disease (SARS-COV-2).

Optional safety goggles (not shown) may be provided to further protect the eyes of the user. A remote wireless monitor 831 with safety alarms is installed to further monitor temperature and as a safety feature.

The prior art of Sabin '861 heat gun 838 preferably has a control panel 841 with a visual display screen 846 and optional finger-operable controls 845a, 845b or other digital touch inputs communicating with an internal microprocessor 833 controlling interlock of temperature gauge sensor (similar to that shown in FIG. 3A) monitoring temperature for adjustment of the amount of heat generating current to raise the heat to a predetermined temperature, and an air pressure sensor to monitor air pressure at a human tolerable level, mimicking air pressure normally provided to a CPAP person patient having sleep apnea or other treatable respiratory obstructive diseases, to treat the person afflicted with the virus causing COVID-19 disease, (SARS-COV-2). Besides being used for treatment of COVID-19 disease, heating the air passing through the heat chambers of the face masks disclosed in FIGS. 1-11, can be done to raise the air temperature to a temperature and relative high humidity sufficiently high to destroy other selected pathogens within the respiratory system of the person. These include other selected pathogens and lung diseases which are selected from the group including bacteria, viruses, fungi, asthma, mesothelioma, lung cancer, dysplasia, chronic obstructive pulmonary disease (COPD), emphysema, chronic bronchitis, pulmonary fibrosis, cystic fibrosis, pneumonia, cancer in general, and heart disease, these alternate treatment regimens further preferably and optionally include the step of controlling the temperature, relative high humidity and elapsed time of the air being heated in the heat chamber by one of either a control box or an app on a smart phone, and providing a microprocessor for handling all communications and readings of a digital Wi-Fi thermometer in the face mask.

Figure 11:
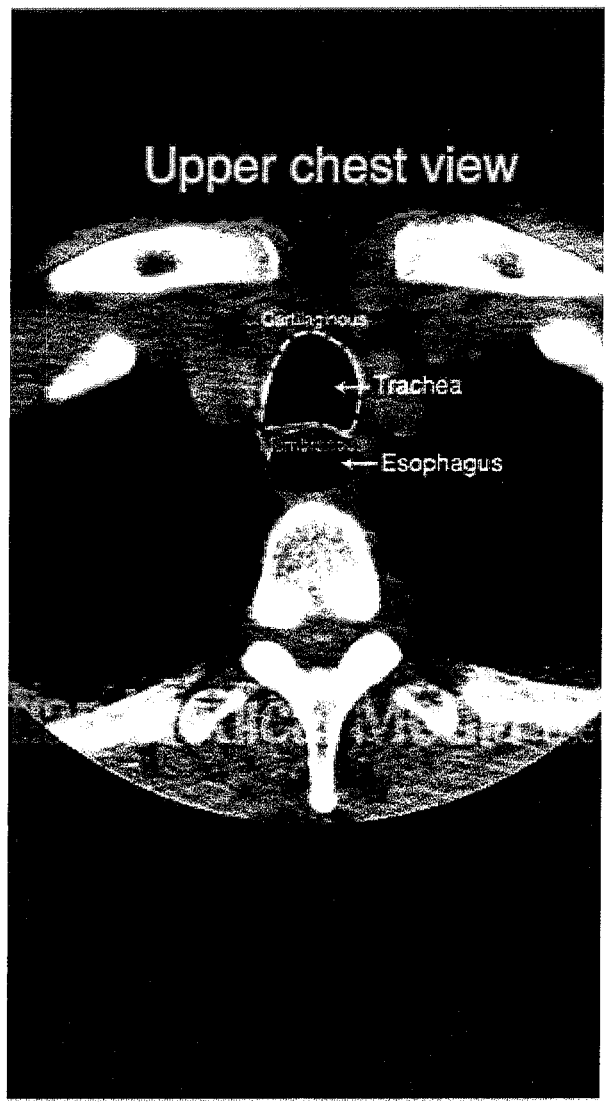
FIG. 11 is a medical scan image showing the thin tracheoesophageal party wall sheath membrane separating the trachea from the adjacent esophagus in a medical patient so that inhaled heat can be transferred via convection across the tracheoesophageal party wall sheath membrane from the trachea into the esophagus, wherein the prior art of Sabin '861 masks of FIGS. 7-10 are used to deliver heated air into the trachea of the medical patient with esophageal cancer.

FIG. 11 is a medical scan image showing the thin tracheoesophageal party wall sheath membrane separating the trachea from the adjacent esophagus in a medical patient so that inhaled heat can be transferred via conduction across the thin tracheoesophageal party wall sheath membrane from the trachea into the esophagus, wherein the prior art of Sabin '861 masks of FIGS. 7-10 are used to deliver heated air into the trachea of the medical patient with esophageal cancer.

The heat from the heater air inspiration through the trachea migrates/transmits/disperses across the tracheoesophageal party wall sheath membrane separating the patient's trachea/windpipe from the esophagus and hits the esophagus with heat.

The heated air will be inspired/inhaled through the mouth and into the trachea/windpipe. Then the trachea and trachea tube under heated constant positive air pressure will then conductively transfer heat through and to the esophagus wall, and to the esophageal tumor.

This is because the esophagus parallels the trachea/windpipe, and the wall of the trachea is very close to the wall the inner wall of the esophagus.

Then it follows by inhaling/inspiring heated air of at least 113 degrees F. with the invention, it is possible enough heat will emanate/traffic from the trachea/windpipe wall and interface with the esophagus wall and esophagus. Therefore the inhaled heat provided at constant air pressure within the trachea migrates across the tracheoesophageal party wall sheath membrane separating the trachea/windpipe from the esophagus and via conduction the inhaled heated air in the trachea/windpipe raises the heat of the localized esophageal tumor at a threshold of about 113 F, which will kill cancer in the esophagus by apoptosis, which is programmed tumor cell death.

In order to non-invasively measure the temperature of the cancer cells being annihilated by apoptosis caused by predetermined time exposure to the conducted heat through the membrane separating the trachea/windpipe from the esophageal tumor site within the esophagus, optionally external probes using external image-based internal body temperature measurements described in Raiko et al, op cit., can be administered such non-invasive devices as ultrasound, magnetic resonance imaging, computed tomography, microwave radiometry, photoacoustic imaging and near-infrared spectrometer, either within a hollow cavity such as CT scan or MRI imaging tunnel machine, or by a hand-held device such as an ultrasound transducer used in combination with a pulsed laser light source provided built into the heat source heat gun, or via a separate handheld measurer such as an ultrasound transducer, where the raised temperature within the tissues of the esophageal tumor can be measured and displayed on a display device, such as on the heat gun or on a display of the remote handheld device or imaging tunnel device.

The prior art of Sabin '861 masks of FIGS. 7-10 are used for treating esophageal cancer in situ with heated air that can be inhaled through a "mister" like asthma inhaler nebulizers, at an elevated temperature less than sauna air temperatures. The inhaled heated air will heat the very thin tracheoesophageal party wall sheath membrane between the esophagus and the respiratory trachea in the throat.

The thin tracheoesophageal party wall sheath membrane therefore can heat the esophageal cancer tumor adjacent to the heated trachea and tracheoesophageal party wall sheath membrane, without the need for sedation of the patient during the invasive procedures currently used surgically. The heated air will be inspired/inhaled through the mouth and into the trachea/windpipe. Then the trachea and trachea tube under heated constant positive pressure will then transfer heat through and to the esophagus wall, and esophagus and tumor.

The esophagus parallels the trachea/windpipe, the wall of the trachea is very close to the wall the inner wall of the esophagus. Then it follows by inhaling/inspiring 113 degrees F. with the invention, it is possible enough heat will emanate/traffic from the trachea/windpipe wall, through the thin tracheoesophageal party wall sheath membrane and interface with the esophagus wall and esophagus. The inhaled heat, when provided at a temperature of about 113 F will kill cancer in the esophagus.

Although the temperature of 113 F will kill the cancer in the esophagus, the heat can be provided at a higher amount, up to about 140-150 F to accommodate any heat loss caused by the presence of the thin tracheoesophageal party wall sheath membrane separating the trachea from the esophagus. However, because of the thinness of the tracheoesophageal party wall sheath membrane separating the esophagus from the trachea, it is assumed that most of the heat will be transferred through the tracheoesophageal party wall sheath membrane to the esophageal tumor.

It is further noted that the patient's trachea and throat can tolerate heat being provided under pressure at an amount significantly less than medically safe inhaled air temperature within a conventional sauna chamber. The LED screen of the heat gun can provide the medical provider with ongoing temperatures of the air going into the trachea so that the patient is not harmed by excess heat than that programmed to treat the targeted esophageal tumor.

It is further noted that preferably the health care practitioner, the patient and/or any assistant may wear protective safety eyeglasses.

In the foregoing description, certain terms and visual depictions are used to illustrate the preferred embodiment. However, no unnecessary limitations are to be construed by the terms used or illustrations depicted, beyond what is shown in the prior art, since the terms and illustrations are exemplary only, and are not meant to limit the scope of the present invention.

It is further known that other modifications may be made to the present invention, without departing the scope of the invention, as noted in the appended Claims.

I claim:

1. A method for treating esophageal cancer in situ with a flow of heated air that can be inhaled through a mask and mouthpiece, comprising the steps of: providing and directing the flow of the heated air from a heat source to be inspired/inhaled through a mouth and into a trachea/windpipe, at an elevated temperature less than sauna air temperatures into the trachea of a patient at a sufficient constant positive pressure and temperature to uniformly heat the patient's tracheoesophageal party wall sheath membrane extending between an esophagus and a respiratory trachea in the patient; monitoring and allowing the heated air to heat the patient's tracheoesophageal party wall sheath membrane at a predetermined temperature and constant positive air pressure through the tracheoesophageal party wall sheath membrane to conductively heat the esophageal cancer adjacent to the heated trachea and the tracheoesophageal party wall sheath membrane; whereby the heat provided at the predetermined temperature and at the constant positive pressure from the heated air is inspired by the patient through the trachea migrates/transmits/disperses conductively across the tracheoesophageal party wall sheath membrane separating the patient trachea from the esophagus to contact the esophageal cancer at the predetermined heat and positive pressure sufficient to cause apoptosis programmed cell death thereat, further comprising the steps of: a) providing a heat gun as said heat source; b) installing a correct outlet nozzle on the heat gun; c) determining and adjusting the temperature of the flow of heated air; d) programing and providing the flow of heated air at said constant positive pressure and at a threshold temperature of the esophageal cancer sufficient to remove the esophageal cancer; e) adjusting the output nozzle of said heat gun and supplying said flow of heated air through the patient's mouth and trachea to a location of the tracheoesophageal party wall sheath membrane separating the trachea from the esophagus in the vicinity of the esophageal cancer f) activating said temperature-controlled heat gun with locks and interlocks for a predetermined time, at which time the entire tumor will be conductively heated across the tracheoesophageal party wall sheath membrane from the trachea into the esophagus with heat derived from said flow of heated air at controlled threshold temperatures; and, g) monitoring the cancer temperature for ensuring that the heated air does not exceed a safe temperature threshold within the trachea and esophagus of the patient.

2. The method of claim 1, wherein said outlet nozzle is sufficiently large and shaped to deliver heat to the esophageal cancer through the tracheoesophageal party wall sheath membrane, separating the trachea from the esophagus.

3. The method of claim 2, wherein a display comprises an LCD screen showing both of said temperatures, including said set programmed temperature and a current temperature within the trachea and esophagus of the patient.

4. The method of claim 3, in which the set programmed temperature is displayed on the screen of the heat gun.

5. The method of claim 3, wherein an efficacious internally applied heated air being delivered to said esophageal cancer located adjacent to the tracheoesophageal party wall sheath membrane, separating the trachea from the esophagus at a range of about 107 to 113 degrees F.

6. The method of claim 5, further comprising the step of inserting a subcutaneous needle probe temperature monitor into the in situ site of the esophageal cancer being treated and measuring the temperature of the cancer being treated.

7. A method for treating esophageal cancer comprising the steps of; a) placing a concentrated but efficacious quantity of heated air generated by a heat source at a constant positive air pressure, within the trachea of a patient adjacent to and spaced from said cancer on and/or extending within the esophagus; b) directing said efficacious applied heated air from said heat source through the trachea to conductively transfer said heated air heat source through the tracheoesophageal party wall sheath membrane to the esophageal cancer adjacent thereto; c) applying said efficacious exterior topically applied heated air directed from said heat source to a full area of said cancer; d) programming said heat source for producing and directing said efficacious exterior topically applied heated air having a temperature sufficient for, and for a sufficient time, to destroy said cancer on and/or extending within the esophagus of the patient; e) monitoring said heat source for insuring that said efficacious inhaled heated air being delivered to said cancer through the tracheoesophageal party wall sheath membrane does not exceed a predetermined safe temperature threshold of said inhaled heated air at a constant positive air pressure; and, f) mounting a display on or adjacent said heat source showing said set programmed temperature and a current temperature of the esophageal cancer being treated, said cancer located within or on the esophagus in the vicinity of the tracheoesophageal party wall sheath membrane separating the esophagus from the trachea of the patient.

* * * * *